(12) United States Patent
Gottesman et al.

(10) Patent No.: US 7,119,193 B2
(45) Date of Patent: Oct. 10, 2006

(54) **IDENTIFICATION OF NEW SMALL RNAS AND ORFS OF *E. COLI* AS MEDIATORS OF CELL AND INTERCELL REGULATION**

(75) Inventors: Susan Gottesman, Bethesda, MD (US); Gisela Storz, Bethesda, MD (US); Francis Repoila, Colomiers (FR); Karen Wassarman, Middleton, WI (US); Carsten Rosenow, Redwood Shores, CA (US)

(73) Assignees: The United States of America as represented by the Department of Health and Human Services, Washington, DC (US); Affymetrix, Inc., Santa Clara, CA (US)

( * ) Notice: Subject to any disclaimer, the term of this patent is extended or adjusted under 35 U.S.C. 154(b) by 342 days.

(21) Appl. No.: 10/627,007

(22) Filed: Jul. 25, 2003

(65) Prior Publication Data

US 2005/0069894 A1    Mar. 31, 2005

Related U.S. Application Data

(63) Continuation of application No. PCT/US02/03147, filed on Jan. 31, 2002.

(60) Provisional application No. 60/266,402, filed on Feb. 1, 2001.

(51) Int. Cl.
*C12N 15/11* (2006.01)

(52) U.S. Cl. .................... 536/24.1; 435/320.1

(58) Field of Classification Search .................... None
See application file for complete search history.

(56) References Cited

OTHER PUBLICATIONS

Result 3, Locus ECOUW67 Accession No. U18997 (Aug. 18, 1999).*
Altschul, S.F. et al. 1990 "Basic local alignment search tool" *J. Mol. Biol.* 215: 403-410.
Altuvia S. et al. 1998 "The *Escherichia coli* OxyS regulatory RNA represses fhlA translation by blocking ribosome binding" *EMBO J.* 17(20):6069-75.
Altuvia, S. et al. 1997 "A small, stable RNA induced by oxidative stress: Role as a pleiotropic regulator and antimutator" *Cell* 90: 43-53.
Argaman, L et al. 2001 "Novel small RNA-encoding genes in the intergenic regions of *Escherichia coli*" *Curr Biol.* 11:941-50.
Bachellier, S. et al. 1996 "Repeated sequences" In: *Escherichia coli* and Salmonella: Cellular and molecular biology (ed. F.C. Neidhardt, et al.), pp. 2012-2040 American Society for Microbiology, Washington, D.C.

Barreiro, V. et al. 1992 "Attachment sites for bacteriophage P2 on the *Escherichia coli* chromosome: DNA sequences, localization on the physical map, and detection of a P2-like remnant in *E. coli* K-12 derivatives" *J. Bacteriol.* 174: 4086-4093.
Blattner, F.R et al. 1997 "The complete genome sequence of *Escherichia coli* K-12" *Science* 277: 1453-1474.
Blattner, F.R et al. 1997 "*Escherichia coli* K12 MG1655 section 122 of 400 of the complete genome" Database EMBL Online Jan. 29, 1997, Database accession No. AE000232.
Blumenthal, T. et al. 1979 "RNA replication: Function and structure of Qβ-replicase" *Annu. Rev. Biochem.* 48: 525-548.
Bouvier, J et al. 1992 "Cloning, characterization, and expression of the *dapE* gene of *Escherichia coli*" *J. Bacteriol.* 174: 5265-5271.
Brown, L. et al. 1996 "Efficient translation of the RpoS sigma factor in *Salmonella typhimurium* requires Host Factor I, an RNA-binding protein encoded by the *hfq* gene" *J. Bacteriol.* 178: 3763-3770.
Campbell, A.M. 1992 "Chromosomal insertion sites for phages and plasmids" *J. Bacteriol.* 174: 7495-7499.
Compan, I. et al. 1994 "Anaerobic activation of *arcA* transcription in *Escherichia coli*: Roles of Fnr and ArcA" *Mol. Microbiol.* 11: 955-964.
Delcher, A.L. et al. 1999 "Improved microbial gene identification with GLIMMER" *Nucleic Acids Res.* 27: 4636-4641.
Devereux, J. et al. 1984 "A comprehensive set of sequence analysis programs for the VAX" *Nucleic Acids Res.* 12: 387-395.
Eddy, S.R. 1999 "Noncoding RNA genes" *Curr. Opin. Genet. Dev.* 9: 695-699.
Franze de Fernandez, M. et al. 1968 "Factor fraction required for the synthesis of bacteriophage Qβ RNA" *Nature* 219: 588-590.
Gelfand, M.S. 1999 "Recognition of regulatory sites by genome comparison" *Res. Microbiol.* 150: 755-771.
Ghisotti, D et al. 1992 "Genetic analysis of the immunity region of phage-plasmid P4" *Mol. Microbiol.* 6: 3405-3413.
Hajndsorf, E. et al. 2000 "Host factor Hfq of *Escherichia coli* stimulates elongation of poly(A) tails by poly(A) polymerase I" *PNAS USA* 97: 1501-1505.
Karzai, A.W et al. 1999 "SmpB, a unique RNA-binding protein essential for the peptide-tagging activity of SsrA (tmRNA)" *EMBO J.* 18:3793-3799.
Kirby, J.E et al. 1994 "Excision of a P4-like cryptic prophage leads to Alp protease expression in *Escherichia coli*" *J. Bacteriol.* 176: 2068-2081.
Lazzzera, B.A. 2000 "Quorum sensing and starvation: signals for entry into stationary phase" *Curr. Opin. Microbiol.* 3: 177-182.

(Continued)

*Primary Examiner*—James Ketter
(74) *Attorney, Agent, or Firm*—Knobbe, Martens, Olson & Bear, LLP

(57) ABSTRACT

The invention relates to new small RNAs and ORFs of *E. coli* as mediators of cell and intercell regulation.

1 Claim, 7 Drawing Sheets

OTHER PUBLICATIONS

Majdelani N. et al. 1998 "DsrA RNA regulates translation of RpoS message by an anti-antisense mechanism, independent of its action as an antisilencer of transcription" *PNAS USA* 95(21):12462-7.

Majdalani, N. et al. 2001 "Regulation of RpoS by a novel small RNA: the characterization of RprA" *Mol. Microbiol.* 39: 1382-1394.

McVeigh, A. et al. 2000 "IS1414, an *Escherichia coli* insertion sequence with a heat-stable enterotoxin gene embedded in a transposase-like gene" *Infect. Immun.* 68: 5710-5715.

Montzka, K.A. et al. 1988 "Additional low-abundance human small nuclear ribonucleoproteins: U11, U12, etc." *PNAS USA* 85: 8885-8889.

Muffler, A. et al. 1996 "The RNA-binding protein HF-I, known as a host factor for phage Qβ RNA replication, is essential for *rpoS* translation in *Escherichia coli*" *Genes & Dev.* 10: 1143-1151.

Okamoto, K. et al. 1986 "Mechanism for the autogenous control of the *crp* operon: Transcriptional inhibition by a divergent RNA transcript" *PNAS USA* 83: 5000-5004.

Pepe, C.M. et al 1997 "Regulation of the "*tetCD*" genes of transposon *Tn10*" *J. Mol. Biol.* 270: 14-25.

Rudd, K.E. 1998 "Linkage map of *Escherichia coli* K-12, edition 10: The physical map" *Microbiol. Mol. Biol. Rev.* 62: 985-1019.

Rudd K.E. 1999 "Novel intergenic repeats of *Escherichia coli* K-12" *Res. Microbiol.* 150: 653-664.

Seoane, A.S. et al. 1995 "Identification of new genes regulated by the *marRAB* operon in *Escherichia coli*" *J. Bacteriol.* 177: 530-535.

Sledjeski D. et al. 1995 "A small RNA acts as an antisilencer of the H-NS-silenced *rcsA* gene of *Escherichia coli*" *PNAS USA* 92(6):2003-7.

Sledjeski, D.D. et al. 1996 "The small RNA, DsrA, is essential for the low teperature expression of RpoS during exponential growth in *Eschericia coli*" *EMBO J.* 15: 3993-4000.

Sledjeski, D.D. et al. 2001 "Hfq is necessary for regulation by the untranslated RNA DsrA" *J. Bacteriol.* 183: 1997-2005.

Tsui, H.-C.T. et al. 1997 "Negative regulation of *mutS* and *mutH* repair gene expression by the Hfq and RpoS global regulators of *Escherichia coli* K-12" *J. Bacteriol.* 179:7476-7487.

Tyc, K. et al. 1989 "U3, U8 and U13 comprise a new class of mammalian snRNPs localized in the cell nucleolus" *EMBO J.* 8: 3113-3119.

Urbanowski, M.L. et al. 2000 "The *gcvB* gene encodes a small untranslated RNA involved in expression of the dipeptide and oligopeptide transport systems in *Escherichia coli*" *Mol. Microbiol.* 37: 856-868.

Vytvytska, O. et al. 1998 "Host Factor I, Hfq, binds to *Escherichia coli ompA* mRNA in a growth-rate dependent fashion and regulates its stability" *PNAS USA* 95: 14118-14123.

Vytvytska, O. et al. 2000 "Hfq (HFI) stimulates *ompA* mRNA decay by interfering with ribosome binding" *Genes & Dev.* 14: 1109-1118.

Wassarman, K.M. et al. 1992 "The low abundance U11 and U12 snRNAs interact to form a two snRNP complex" *Mol. Cell. Biol.* 12: 1276-1285.

Wassarman, K.M. et al. 1999 "Small RNAs in *Escherichia coli*" *Trends Microbiol.* 7: 37-45.

Wassarman, K.M. et al., G. 2000 "6S RNA regulates *E. coli* RNA polymerase activity" *Cell* 101: 613-623.

Wassarman K.M. et al. 2001 "Identification of novel small RNAs using comparitive genomics and microarrays" *Genes Dev.* 15(13): 1637-51.

Zhang, A. et al. 1998 "The oxyS regulatory RNA represses *rpoS* translation by binding Hfq (HF-1) protein" *EMBO J.* 17: 6061-6068.

Zhou, Y.-N. & Gottesman, S. 1998 "Regulation of proteolysis of the stationary-phase sigma factor RpoS" *J. Bacteriol.* 180: 1154-1158.

Rudd, K.E. 1999 "Novel intergenic repeats of *Escherichia coli* K-12", *Res. Microbiol.* 150:653-664.

* cited by examiner rprA csrB oxyS

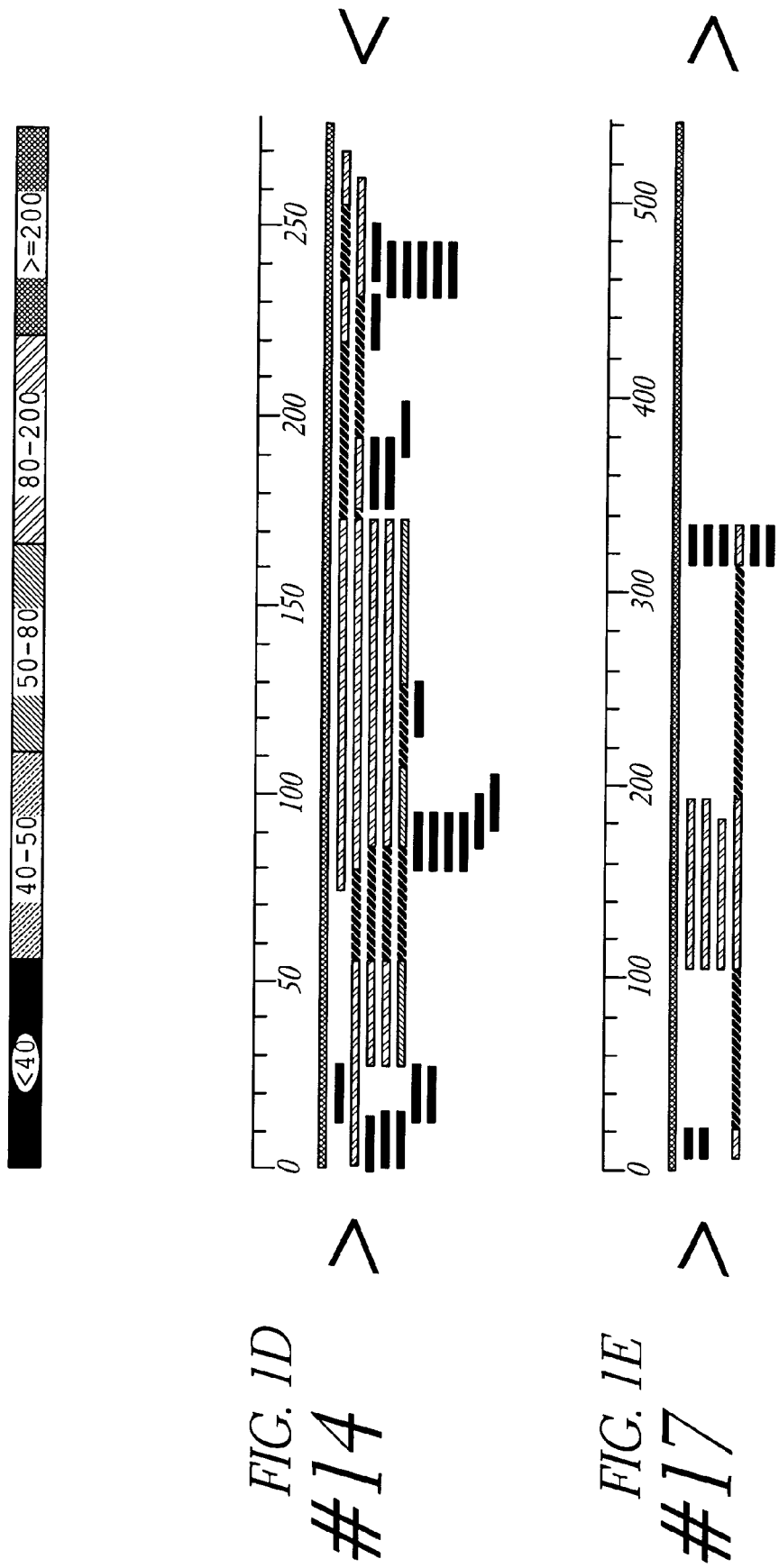
FIG. 1D #14
FIG. 1E #17

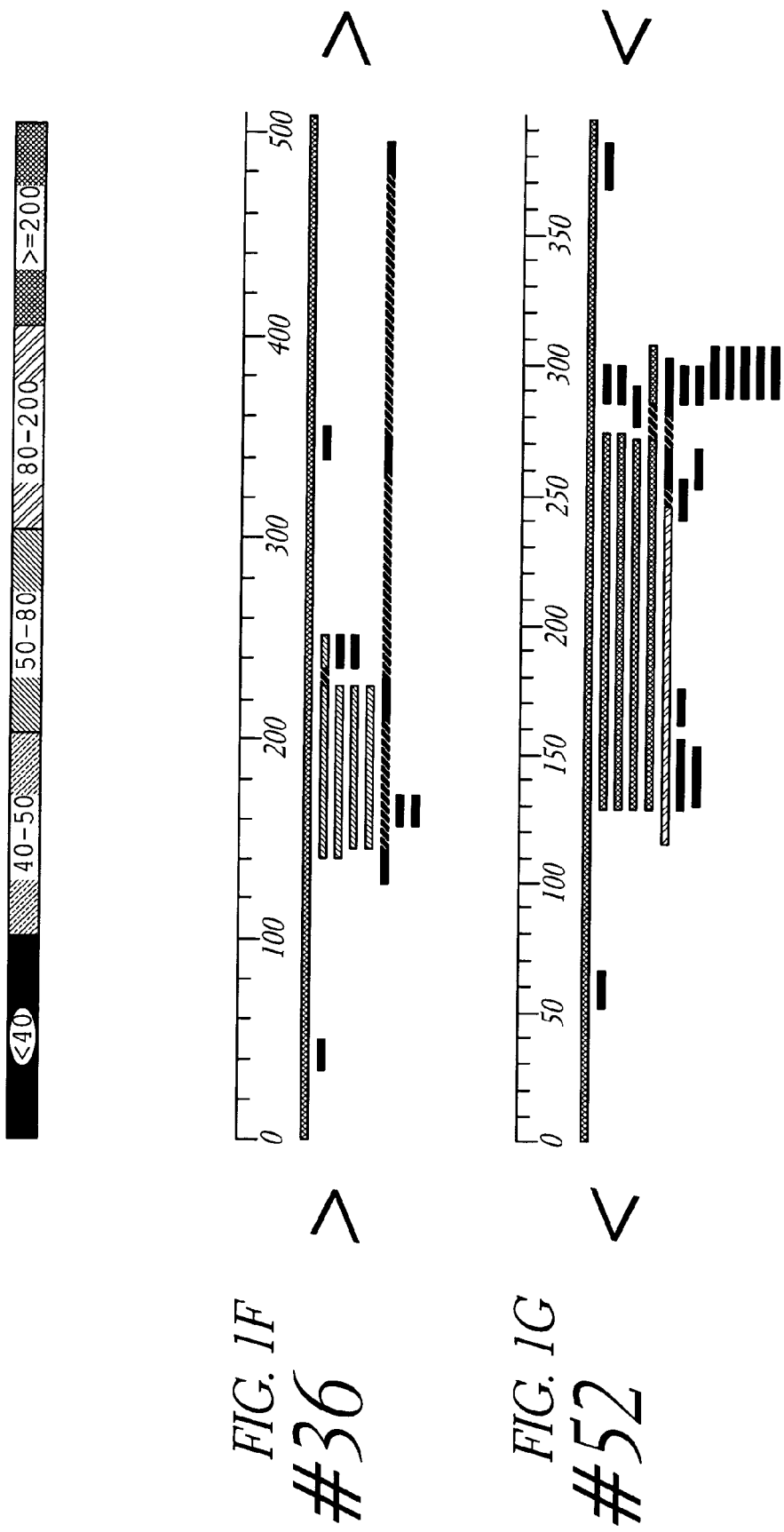
FIG. 1F #36
FIG. 1G #52

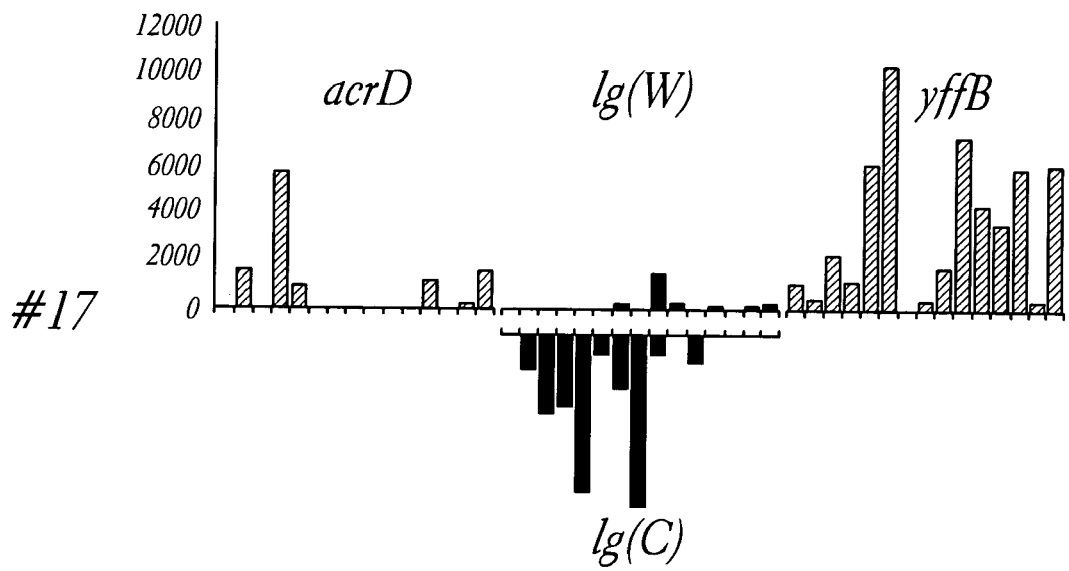
FIG. 2D #17
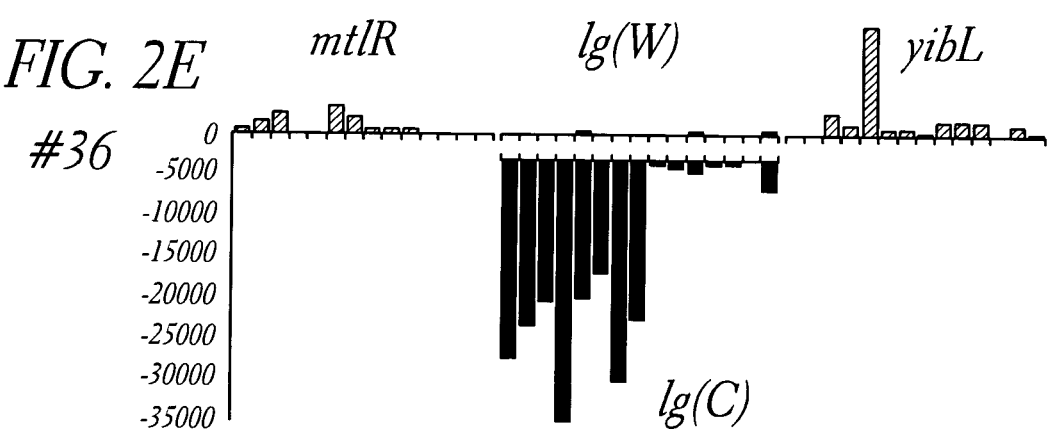
FIG. 2E #36
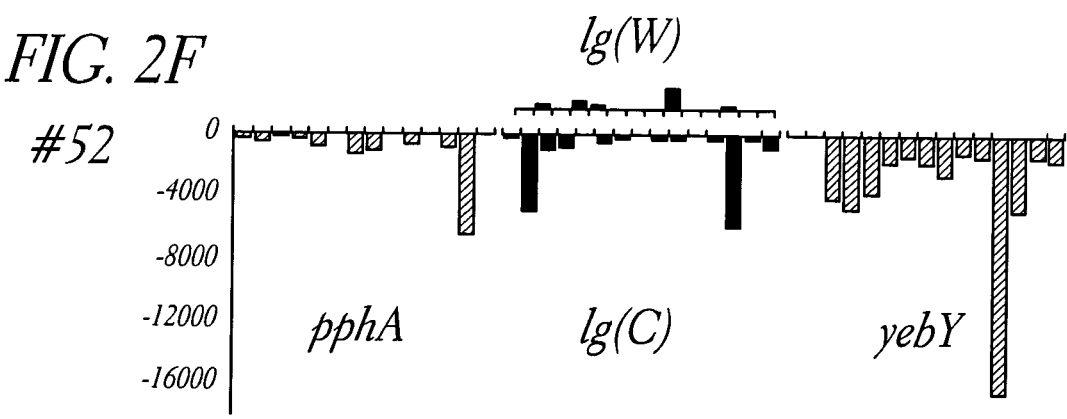
FIG. 2F #52

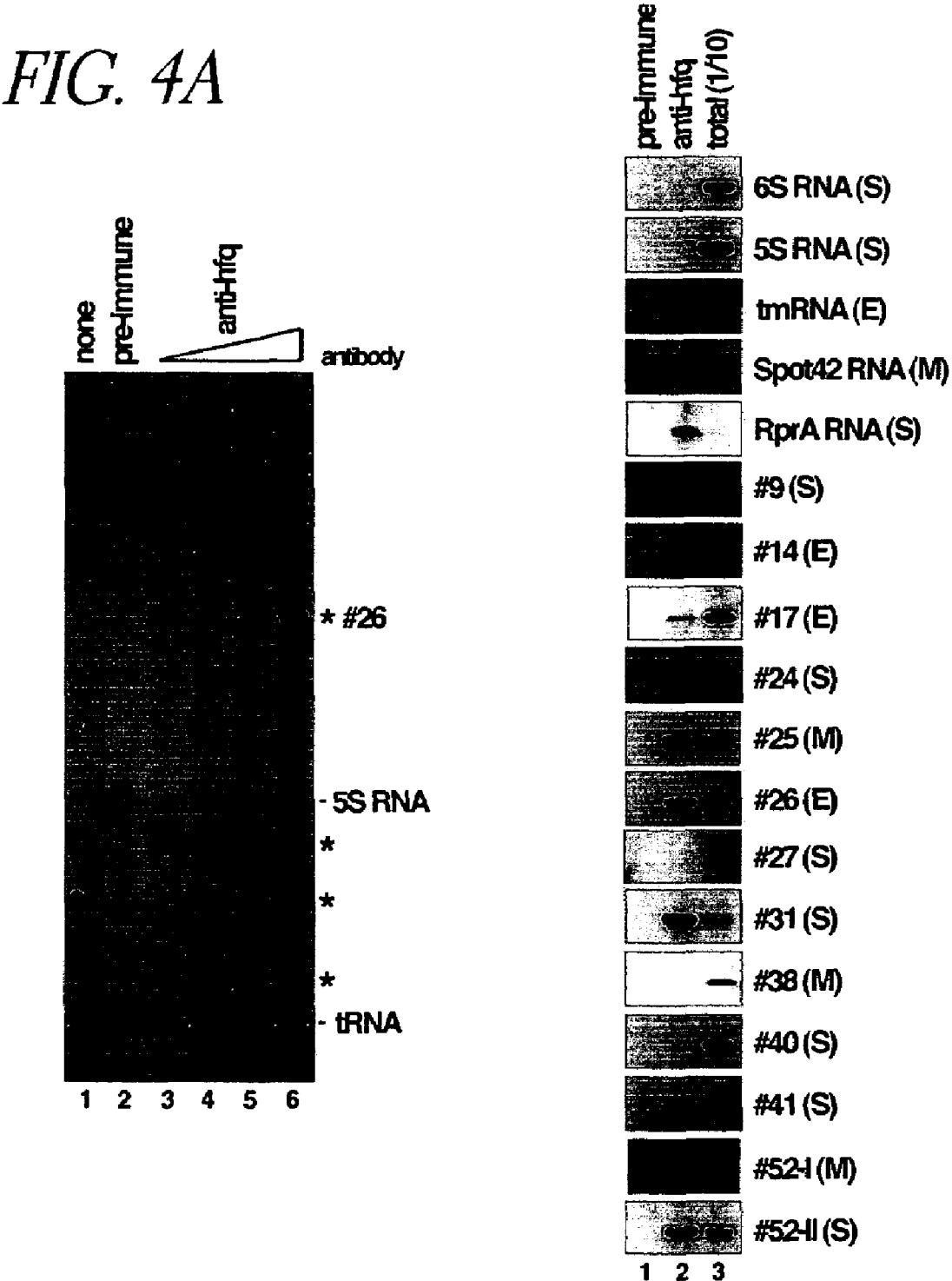

SEQUENCE LISTING

<160> NUMBER OF SEQ ID NOS: 161

<210> SEQ ID NO 1
<211> LENGTH: 93
<212> TYPE: DNA
<213> ORGANISM: E. Coli

<400> SEQUENCE: 1
gccccttcaa gagctaagcc actgagagtg ccggagataa gcgccggatg gggtagaaac     60
ccttaagcct gtgtcgcaca gacttaaggg ttt                                  93

<210> SEQ ID NO 2
<211> LENGTH: 86
<212> TYPE: DNA
<213> ORGANISM: E. Coli

<400> SEQUENCE: 2
tcgctgaaaa acataaccca taaatgcta gctgtaccag gaaccacctc cttagcctgt      60
gtaatctccc ttacacgggc ttattt                                          86

<210> SEQ ID NO 3
<211> LENGTH: 307
<212> TYPE: DNA
<213> ORGANISM: E. Coli

<400> SEQUENCE: 3
actgcggccc tttccgccgt ctcgcaaacg ggcgctggct ttaggaaagg atgttccgtg     60
ccgtaaatgc aggtgtttca cagcgcttgc tatcgcggca atatcgccag tggtgctgtc   120
gtgatgcggt cttcgcatgg accgcacaat gaagatacgg tgcttttgta tcgtacttat   180
tgtttctggt gcgctgttaa ccgaggtaaa taataaccgg agtctctccg gcgacaattt   240
actggtggtt aacaaccttc agagcagcaa gtaagcccga atgccgccct ttgggcggca   300
tatttta                                                             307

<210> SEQ ID NO 4
<211> LENGTH: 65
<212> TYPE: DNA
<213> ORGANISM: E. Coli

<400> SEQUENCE: 4
acggcgcagc caagatttcc ctggtgttgg cgcagtattc gcgcaccccg gtctagccgg     60
ggtca                                                                65

<210> SEQ ID NO 5
<211> LENGTH: 92
<212> TYPE: DNA
<213> ORGANISM: E. Coli

<400> SEQUENCE: 5
cgcgatcagg aagaccctcg cggagaacct gaaagcacga cattgctcac attgcttcca     60
gtattactta gccagccggg tgctggcttt tt                                   92

<210> SEQ ID NO 6
<211> LENGTH: 211
<212> TYPE: DNA
<213> ORGANISM: E. Coli

<400> SEQUENCE: 6

```
aacgagtaga tgctcattcc atctcttatg ttcgccttag tgcctcataa actccggaat     60
gacgcagagc cgtttacggt gcttatcgtc cactgacaga tgtcgcttat gcctcatcag    120
acaccatgga cacaacgttg agtgaagcac ccacttgttg tcatacagac ctgttttaac    180
gcctgctccg taataagagc aggcgttttt t                                   211

<210> SEQ ID NO 7
<211> LENGTH: 141
<212> TYPE: DNA
<213> ORGANISM: E. Coli

<400> SEQUENCE: 7
catcaacacc aaccggaacc tccaccacgt gctcgaatga ggtgtgttga cgtcggggga     60
aaccctcctg tgtaccagcg ggatagagag aaagacaaag accggaaaac aaactaaagc    120
gcccttgtgg cgctttagtt t                                              141

<210> SEQ ID NO 8
<211> LENGTH: 79
<212> TYPE: DNA
<213> ORGANISM: E. Coli

<400> SEQUENCE: 8
tgccactgct tttctttgat gtccccattt tgtggagccc atcaaccccg ccatttcggt     60
tcaaggttga tgggttttt                                                  79

<210> SEQ ID NO 9
<211> LENGTH: 272
<212> TYPE: DNA
<213> ORGANISM: E. Coli

<400> SEQUENCE: 9
tgtttaaagc aaaggcgtaa agtagcaccc atagagcgag gacgctaaca ggaacaatga     60
ctcaggatga gggtcaggag cgccaggagg cgaagacaga ggattgtcag gaagacaaac    120
gtccggagac gtaattaaac ggaaatggaa tcaacacgga ttgttcccta aggaaaaac    180 agggtgtgtt ggcggcctgc aaggattgta agacccgtta agggttatga gtcaggaaaa    240
aaggcgacag agtaatctgt cgccttttt ct                                   272

<210> SEQ ID NO 10
<211> LENGTH: 195
<212> TYPE: DNA
<213> ORGANISM: E. Coli

<400> SEQUENCE: 10
acattgtaaa ccagagttgc gaaggtacaa aaaattaacg ttttagcaat agctatataa     60
tatagcctgt gctatatctg tatgtaatgc aatcatccct caaggatcga cgggattagc    120
aagtcaggag gtcttatgaa tgagttcaag aggtgtatgc gcgtgtttag tcattctccc    180
tttaaagtac ggtta                                                     195

<210> SEQ ID NO 11
<211> LENGTH: 82
<212> TYPE: DNA
<213> ORGANISM: E. Coli

<400> SEQUENCE: 11
atcccagagg tattgatagg tgaagtcaac ttcgggttga gcacatgaat tacaccagcc     60
```
tgcgcagatg cgcaggtttt tt                                          82

<210> SEQ ID NO 12
<211> LENGTH: 92
<212> TYPE: DNA
<213> ORGANISM: E. Coli

<400> SEQUENCE: 12
atcccagagg tattgattgg tgagattatt cggtacgctc tcttcgtacc ctgtctcttg    60
caccaacctg cgcggatgcg caggtttttt tt                                  92

<210> SEQ ID NO 13
<211> LENGTH: 278
<212> TYPE: DNA
<213> ORGANISM: E. Coli

<400> SEQUENCE: 13
actataaagt cagcgaagga aatgcttctg gcttttaaca gataaaaaga gaccgaacac    60
gattcctgta ttcggtccag ggaaatggct cttgggagag agccgtgcgc taaaagttgg   120
cattaatgca ggcttagttg ccttgccctt taagaataga tgacgacgcc aggttttcca   180
gtttgcgtgc aaaatggtca ataaaaagcg tggtggtcat cagctgaaat gttaaaaacc   240
gcccgttctg gtgaaagaac tgaggcggtt tttttatt                           278

<210> SEQ ID NO 14
<211> LENGTH: 105
<212> TYPE: DNA
<213> ORGANISM: E. Coli

<400> SEQUENCE: 14
agggcaaggc aactaagcct gcattaatgc caacttttag cgcacggctc tctcccaaga    60
gccatttccc tggaccgaat acaggaatcg tgttcggtct ctttt                   105

<210> SEQ ID NO 15
<211> LENGTH: 144
<212> TYPE: DNA
<213> ORGANISM: E. Coli

<400> SEQUENCE: 15
agtgagggtt agggagaggt ttcccccctcc ccctggtgtt cttagtaagc ctggaagcta    60
atcactaaga gtatcaccag tatgatgacg tgcttcatca taaccctttc cttattaaaa   120
gccctcttct ccgggagagg cttt                                          144

<210> SEQ ID NO 16
<211> LENGTH: 137
<212> TYPE: DNA
<213> ORGANISM: E. Coli

<400> SEQUENCE: 16
agtgagggta gagcggggtt tccccgccc tggtagtctt agtaagcggg gaagcttatg     60
actaagagca ccacgatgat gagtagcttc atcatgaccc tttccttatt tatggcccct   120
tcctcgggag gggcttt                                                  137

<210> SEQ ID NO 17
<211> LENGTH: 112
<212> TYPE: DNA
<213> ORGANISM: E. Coli

<400> SEQUENCE: 17

```
aggaacaagg gtaagggagg atttctcccc cctctgattg gctgttaata agctgcgaaa        60
cttacgagta acaacacaat cagtatgatg acgagcttca tcataaccct tt              112

<210> SEQ ID NO 18
<211> LENGTH: 139
<212> TYPE: DNA
<213> ORGANISM: E. Coli

<400> SEQUENCE: 18
cagggcaata tctctcttgc aggtgaatgc aacgtcaagc gatgggcgtt gcgctccata        60
ttgtcttact tccttttttg aattactgca tagcacaatt gattcgtacg acgccgactt       120
tgatgagtcg gcttttttt                                                   139

<210> SEQ ID NO 19
<211> LENGTH: 155
<212> TYPE: DNA
<213> ORGANISM: E. Coli

<400> SEQUENCE: 19
tagagtaaag gaacaagggt aagggaggat ttctcccccc tctgattggc tgttaataag        60
ctgcgaaact tacgagtaac aacacaatca gtatgatgac gagcttcatc ataacccttt       120
ccttctgtaa ggccccttc ttcgggaggg gcttt                                  155

<210> SEQ ID NO 20
<211> LENGTH: 128
<212> TYPE: DNA
<213> ORGANISM: E. Coli

<400> SEQUENCE: 20 catagggca atgataaaag gtggcaaaaa tgaatgtttc cagtagaact gtagtactga         60
taaatttctt tgctgctgtt ggtttgttta ctcttatctc tatgagattt ggctggttta       120
tttgatgt                                                               128

<210> SEQ ID NO 21
<211> LENGTH: 31
<212> TYPE: PRT
<213> ORGANISM: E. Coli

<400> SEQUENCE: 21

Met Asn Val Ser Ser Arg Thr Val Val Leu Ile Asn Phe Phe Ala Ala
 1               5                  10                  15

Val Gly Leu Phe Thr Leu Ile Ser Met Arg Phe Gly Trp Phe Ile
                20                  25                  30

<210> SEQ ID NO 22
<211> LENGTH: 84
<212> TYPE: DNA
<213> ORGANISM: E. Coli

<400> SEQUENCE: 22
ataattataa gagaggttgt tatgattgaa cgtgaactgg ggaactggaa agactttatc        60
gaagttatgc ttcgtaagta attc                                              84

<210> SEQ ID NO 23
<211> LENGTH: 19
<212> TYPE: PRT
<213> ORGANISM: E. Coli
```

-continued

<400> SEQUENCE: 23

Met Ile Glu Arg Glu Leu Gly Asn Trp Lys Asp Phe Ile Glu Val Met
1               5                   10                  15

Leu Arg Lys

<210> SEQ ID NO 24
<211> LENGTH: 180
<212> TYPE: DNA
<213> ORGANISM: E. Coli

<400> SEQUENCE: 24
aaaggagacg cttatgtttc gttggggcat catatttctg gttatcgcgt taatcgccgc      60
cgcacttggg tttggtggtc tggccggtac cgctgcaggc gcagctaaaa ttgtctttgt     120
cgtcgggatt attctgttcc tggtgagttt gttcatgggc cgaaaacgac cctagatttc     180

<210> SEQ ID NO 25
<211> LENGTH: 53
<212> TYPE: PRT
<213> ORGANISM: E. Coli

<400> SEQUENCE: 25

Met Phe Arg Trp Gly Ile Ile Phe Leu Val Ile Ala Leu Ile Ala Ala
1               5                   10                  15

Ala Leu Gly Phe Gly Gly Leu Ala Gly Thr Ala Ala Gly Ala Ala Lys
                20                  25                  30

Ile Val Phe Val Val Gly Ile Ile Leu Phe Leu Val Ser Leu Phe Met
            35                  40                  45

Gly Arg Lys Arg Pro
    50

<210> SEQ ID NO 26
<211> LENGTH: 226
<212> TYPE: DNA
<213> ORGANISM: E. Coli

<400> SEQUENCE: 26
atacggagat atcatcatgg gcaaattagg tgaaaacgtt ccgcttctta tcgataaagc      60
cgtagatttc atggcatcaa gccaggcgtt ccgggagtat ctgaaaaaac ttcctccccg     120
taacgcgatt ccgtccggaa tacccgatga agcgtgccg ttatatctac aacgtctgga     180
gtattatcgt cggctttatc ggccgaagca ggtagagggg cagtaa                    226

<210> SEQ ID NO 27
<211> LENGTH: 69
<212> TYPE: PRT
<213> ORGANISM: E. Coli

<400> SEQUENCE: 27

Met Gly Lys Leu Gly Glu Asn Val Pro Leu Leu Ile Asp Lys Ala Val
1               5                   10                  15

Asp Phe Met Ala Ser Ser Gln Ala Phe Arg Glu Tyr Leu Lys Lys Leu
                20                  25                  30

Pro Pro Arg Asn Ala Ile Pro Ser Gly Ile Pro Asp Glu Ser Val Pro
            35                  40                  45

Leu Tyr Leu Gln Arg Leu Glu Tyr Tyr Arg Arg Leu Tyr Arg Pro Lys
        50                  55                  60

Gln Val Glu Gly Gln
65

<210> SEQ ID NO 28
<211> LENGTH: 189
<212> TYPE: DNA
<213> ORGANISM: E. Coli

<400> SEQUENCE: 28

```
gagtagttaa catgaagcgg agtagaacgg aagtggggcg ctggcgcatg cagcgtcagg      60
ctagccgacg taaatcgcgt tggcttgagg ggcaatcgcg ccgaaatatg cgtatccaca     120
gcatcaggaa gtgcattcta acaaacagc gtaactcgtt attgtttgcg atctacaata     180
tctaaatgt                                                             189
```

<210> SEQ ID NO 29
<211> LENGTH: 57
<212> TYPE: PRT
<213> ORGANISM: E. Coli

<400> SEQUENCE: 29

```
Met Lys Arg Ser Arg Thr Glu Val Gly Arg Trp Arg Met Gln Arg Gln
 1               5                  10                  15

Ala Ser Arg Arg Lys Ser Arg Trp Leu Glu Gly Gln Ser Arg Arg Asn
            20                  25                  30

Met Arg Ile His Ser Ile Arg Lys Cys Ile Leu Asn Lys Gln Arg Asn
        35                  40                  45

Ser Leu Leu Phe Ala Ile Tyr Asn Ile
    50                  55
```

<210> SEQ ID NO 30
<211> LENGTH: 117
<212> TYPE: DNA
<213> ORGANISM: E. Coli

<400> SEQUENCE: 30

```
aacggaggca aataatgctg ggtaatatga atgtttttat ggccgtactg ggaataattt      60
tattttctgg ttttctggcc gcgtatttca gccacaaatg ggatgactaa tgaacgg        117
```

<210> SEQ ID NO 31
<211> LENGTH: 31
<212> TYPE: PRT
<213> ORGANISM: E. Coli

<400> SEQUENCE: 31

```
Met Leu Gly Asn Met Asn Val Phe Met Ala Val Leu Gly Ile Ile Leu
 1               5                  10                  15

Phe Ser Gly Phe Leu Ala Ala Tyr Phe Ser His Lys Trp Asp Asp
            20                  25                  30
```

<210> SEQ ID NO 32
<211> LENGTH: 25
<212> TYPE: DNA
<213> ORGANISM: Artificial Sequence
<220> FEATURE:
<223> OTHER INFORMATION: Oligonucleotide

<400> SEQUENCE: 32

```
gcgcctcgtt atcatccaaa atacg                                            25
```

<210> SEQ ID NO 33
<211> LENGTH: 25
<212> TYPE: DNA

```
<213> ORGANISM: Artificial Sequence
<220> FEATURE:
<223> OTHER INFORMATION: Oligonucleotide

<400> SEQUENCE: 33
gtcgcccagc caatgctttc agtcg                                              25

<210> SEQ ID NO 34
<211> LENGTH: 25
<212> TYPE: DNA
<213> ORGANISM: Artificial Sequence
<220> FEATURE:
<223> OTHER INFORMATION: Oligonucleotide

<400> SEQUENCE: 34
attgatcgca cacctgacag ctgcc                                              25

<210> SEQ ID NO 35
<211> LENGTH: 25
<212> TYPE: DNA
<213> ORGANISM: Artificial Sequence
<220> FEATURE:
<223> OTHER INFORMATION: Oligonucleotide

<400> SEQUENCE: 35
gttgtcaccc tggacctggt cgtac                                              25

<210> SEQ ID NO 36
<211> LENGTH: 23
<212> TYPE: DNA
<213> ORGANISM: Artificial Sequence
<220> FEATURE:
<223> OTHER INFORMATION: Oligonucleotide

<400> SEQUENCE: 36
tgaccgcgat ttgcacaaaa tgc                                                23

<210> SEQ ID NO 37
<211> LENGTH: 27
<212> TYPE: DNA
<213> ORGANISM: Artificial Sequence
<220> FEATURE:
<223> OTHER INFORMATION: Oligonucleotide

<400> SEQUENCE: 37
actcttaaat ttcctatcaa aactcgc                                            27

<210> SEQ ID NO 38
<211> LENGTH: 27
<212> TYPE: DNA
<213> ORGANISM: Artificial Sequence
<220> FEATURE:
<223> OTHER INFORMATION: Oligonucleotide

<400> SEQUENCE: 38
ggtattttca gagattatga attgccg                                            27

<210> SEQ ID NO 39
<211> LENGTH: 25
<212> TYPE: DNA
<213> ORGANISM: Artificial Sequence
<220> FEATURE:
<223> OTHER INFORMATION: Oligonucleotide

<400> SEQUENCE: 39
tcacctctcc ttcgagcgct actgg                                              25
```

<210> SEQ ID NO 40
<211> LENGTH: 26
<212> TYPE: DNA
<213> ORGANISM: Artificial Sequence
<220> FEATURE:
<223> OTHER INFORMATION: Oligonucleotide

<400> SEQUENCE: 40
aatgctctcc tgataatgtt aaactt                                  26

<210> SEQ ID NO 41
<211> LENGTH: 26
<212> TYPE: DNA
<213> ORGANISM: Artificial Sequence
<220> FEATURE:
<223> OTHER INFORMATION: Oligonucleotide

<400> SEQUENCE: 41
ggttagctcc gaagcaaaag ccggat                                  26

<210> SEQ ID NO 42
<211> LENGTH: 25
<212> TYPE: DNA
<213> ORGANISM: Artificial Sequence
<220> FEATURE:
<223> OTHER INFORMATION: Oligonucleotide

<400> SEQUENCE: 42
taattccttt caaatgaaac ggagc                                   25

<210> SEQ ID NO 43
<211> LENGTH: 24
<212> TYPE: DNA
<213> ORGANISM: Artificial Sequence
<220> FEATURE:
<223> OTHER INFORMATION: Oligonucleotide

<400> SEQUENCE: 43
ggactccctc attataatta ctgg                                    24

<210> SEQ ID NO 44
<211> LENGTH: 27
<212> TYPE: DNA
<213> ORGANISM: Artificial Sequence
<220> FEATURE:
<223> OTHER INFORMATION: Oligonucleotide

<400> SEQUENCE: 44
ctccttaaac aaggacatta gtctacg                                 27

<210> SEQ ID NO 45
<211> LENGTH: 27
<212> TYPE: DNA
<213> ORGANISM: Artificial Sequence
<220> FEATURE:
<223> OTHER INFORMATION: Oligonucleotide

<400> SEQUENCE: 45
attcacctta cctaatttga ttcttcc                                 27

<210> SEQ ID NO 46
<211> LENGTH: 27
<212> TYPE: DNA
<213> ORGANISM: Artificial Sequence
<220> FEATURE:

<223> OTHER INFORMATION: Oligonucleotide

<400> SEQUENCE: 46
ccatcgcttg acgttgcatt cacctgc    27

<210> SEQ ID NO 47
<211> LENGTH: 26
<212> TYPE: DNA
<213> ORGANISM: Artificial Sequence
<220> FEATURE:
<223> OTHER INFORMATION: Oligonucleotide

<400> SEQUENCE: 47
gtcggcgtcg tacgaatcaa ttgtgc    26

<210> SEQ ID NO 48
<211> LENGTH: 26
<212> TYPE: DNA
<213> ORGANISM: Artificial Sequence
<220> FEATURE:
<223> OTHER INFORMATION: Oligonucleotide

<400> SEQUENCE: 48
gcacaattga ttcgtacgac gccgac    26

<210> SEQ ID NO 49
<211> LENGTH: 25
<212> TYPE: DNA
<213> ORGANISM: Artificial Sequence
<220> FEATURE:
<223> OTHER INFORMATION: Oligonucleotide

<400> SEQUENCE: 49
taaggataat attgcagatc gtaag    25

<210> SEQ ID NO 50
<211> LENGTH: 22
<212> TYPE: DNA
<213> ORGANISM: Artificial Sequence
<220> FEATURE:
<223> OTHER INFORMATION: Oligonucleotide

<400> SEQUENCE: 50
atcatcaaac agcaacttgc cc    22

<210> SEQ ID NO 51
<211> LENGTH: 26
<212> TYPE: DNA
<213> ORGANISM: Artificial Sequence
<220> FEATURE:
<223> OTHER INFORMATION: Oligonucleotide

<400> SEQUENCE: 51
tgtccttctc ctgcaagaga attatt    26

<210> SEQ ID NO 52
<211> LENGTH: 26
<212> TYPE: DNA
<213> ORGANISM: Artificial Sequence
<220> FEATURE:
<223> OTHER INFORMATION: Oligonucleotide

<400> SEQUENCE: 52
gctaataata atgtcttttt cgctcc    26

<210> SEQ ID NO 53
<211> LENGTH: 31
<212> TYPE: DNA
<213> ORGANISM: Artificial Sequence
<220> FEATURE:
<223> OTHER INFORMATION: Oligonucleotide

<400> SEQUENCE: 53
gcttttgtga attaatttgt atatcgaagc g                          31

<210> SEQ ID NO 54
<211> LENGTH: 28
<212> TYPE: DNA
<213> ORGANISM: Artificial Sequence
<220> FEATURE:
<223> OTHER INFORMATION: Oligonucleotide

<400> SEQUENCE: 54
tattaatacc ctctagattg agttaatc                              28

<210> SEQ ID NO 55
<211> LENGTH: 27
<212> TYPE: DNA
<213> ORGANISM: Artificial Sequence
<220> FEATURE:
<223> OTHER INFORMATION: Oligonucleotide

<400> SEQUENCE: 55
cgatttacct cacttcatcg ctttcag                               27

<210> SEQ ID NO 56
<211> LENGTH: 26
<212> TYPE: DNA
<213> ORGANISM: Artificial Sequence
<220> FEATURE:
<223> OTHER INFORMATION: Oligonucleotide

<400> SEQUENCE: 56
tgatcctgac ttaatgccgc aagttc                                26

<210> SEQ ID NO 57
<211> LENGTH: 39
<212> TYPE: DNA
<213> ORGANISM: Artificial Sequence
<220> FEATURE:
<223> OTHER INFORMATION: Oligonucleotide

<400> SEQUENCE: 57
gcttatctcc ggcactctca gtggcttagc tcttgaagg                  39

<210> SEQ ID NO 58
<211> LENGTH: 28
<212> TYPE: DNA
<213> ORGANISM: Artificial Sequence
<220> FEATURE:
<223> OTHER INFORMATION: Oligonucleotide

<400> SEQUENCE: 58
ttgctcacat ctcactttaa tcgtgctc                              28

<210> SEQ ID NO 59
<211> LENGTH: 34
<212> TYPE: DNA
<213> ORGANISM: Artificial Sequence
<220> FEATURE:
<223> OTHER INFORMATION: Oligonucleotide

```
<400> SEQUENCE: 59
atattccacc agctatttgt tagtgaataa aagg                            34

<210> SEQ ID NO 60
<211> LENGTH: 30
<212> TYPE: DNA
<213> ORGANISM: Artificial Sequence
<220> FEATURE:
<223> OTHER INFORMATION: Oligonucleotide

<400> SEQUENCE: 60
tgattaattt cgattatttt tcccggatgg                                 30

<210> SEQ ID NO 61
<211> LENGTH: 28
<212> TYPE: DNA
<213> ORGANISM: Artificial Sequence
<220> FEATURE:
<223> OTHER INFORMATION: Oligonucleotide

<400> SEQUENCE: 61
attagaaaca ggaagcccct cagtcgag                                   28

<210> SEQ ID NO 62
<211> LENGTH: 30
<212> TYPE: DNA
<213> ORGANISM: Artificial Sequence
<220> FEATURE:
<223> OTHER INFORMATION: Oligonucleotide

<400> SEQUENCE: 62
ttattttccc cggaagcaca ttcacttcac                                 30

<210> SEQ ID NO 63
<211> LENGTH: 24
<212> TYPE: DNA
<213> ORGANISM: Artificial Sequence
<220> FEATURE:
<223> OTHER INFORMATION: Oligonucleotide

<400> SEQUENCE: 63
tgatctattg cacaacgagg aagc                                       24

<210> SEQ ID NO 64
<211> LENGTH: 30
<212> TYPE: DNA
<213> ORGANISM: Artificial Sequence
<220> FEATURE:
<223> OTHER INFORMATION: Oligonucleotide

<400> SEQUENCE: 64
tgcttactca tcaaaagtag cgccagattc                                 30

<210> SEQ ID NO 65
<211> LENGTH: 27
<212> TYPE: DNA
<213> ORGANISM: Artificial Sequence
<220> FEATURE:
<223> OTHER INFORMATION: Oligonucleotide

<400> SEQUENCE: 65
taatcgacgg acgatagata attcctg                                    27

<210> SEQ ID NO 66
<211> LENGTH: 28
```

```
<212> TYPE: DNA
<213> ORGANISM: Artificial Sequence
<220> FEATURE:
<223> OTHER INFORMATION: Oligonucleotide

<400> SEQUENCE: 66
ccaatgtgtc gccttttca actttccg                                              28

<210> SEQ ID NO 67
<211> LENGTH: 33
<212> TYPE: DNA
<213> ORGANISM: Artificial Sequence
<220> FEATURE:
<223> OTHER INFORMATION: Oligonucleotide

<400> SEQUENCE: 67
cgatttatga gaataaatac tcatttaagg gtg                                        33

<210> SEQ ID NO 68
<211> LENGTH: 25
<212> TYPE: DNA
<213> ORGANISM: Artificial Sequence
<220> FEATURE:
<223> OTHER INFORMATION: Oligonucleotide

<400> SEQUENCE: 68
aaatccgact ttagttacaa catac                                                 25

<210> SEQ ID NO 69
<211> LENGTH: 26
<212> TYPE: DNA
<213> ORGANISM: Artificial Sequence
<220> FEATURE:
<223> OTHER INFORMATION: Oligonucleotide

<400> SEQUENCE: 69
gaccagacct tcttgatgat gggcac                                                26

<210> SEQ ID NO 70
<211> LENGTH: 24
<212> TYPE: DNA
<213> ORGANISM: Artificial Sequence
<220> FEATURE:
<223> OTHER INFORMATION: Oligonucleotide

<400> SEQUENCE: 70
cgacctcaat tccacgggat ctgg                                                  24

<210> SEQ ID NO 71
<211> LENGTH: 25
<212> TYPE: DNA
<213> ORGANISM: Artificial Sequence
<220> FEATURE:
<223> OTHER INFORMATION: Oligonucleotide

<400> SEQUENCE: 71
atttagctgt agtaatcact cgccg                                                 25

<210> SEQ ID NO 72
<211> LENGTH: 23
<212> TYPE: DNA
<213> ORGANISM: Artificial Sequence
<220> FEATURE:
<223> OTHER INFORMATION: Oligonucleotide

<400> SEQUENCE: 72
```

```
ggtctcctta gcgccttatt gcg                                              23

<210> SEQ ID NO 73
<211> LENGTH: 27
<212> TYPE: DNA
<213> ORGANISM: Artificial Sequence
<220> FEATURE:
<223> OTHER INFORMATION: Oligonucleotide

<400> SEQUENCE: 73
cgcccacatg ctgttcttat tattccc                                          27

<210> SEQ ID NO 74
<211> LENGTH: 24
<212> TYPE: DNA
<213> ORGANISM: Artificial Sequence
<220> FEATURE:
<223> OTHER INFORMATION: Oligonucleotide

<400> SEQUENCE: 74
tttatgacac ctgccactgc cgtc                                             24

<210> SEQ ID NO 75
<211> LENGTH: 30
<212> TYPE: DNA
<213> ORGANISM: Artificial Sequence
<220> FEATURE:
<223> OTHER INFORMATION: Oligonucleotide

<400> SEQUENCE: 75
ctgtcaagtt atctgtttgt taagtcaagc                                       30

<210> SEQ ID NO 76
<211> LENGTH: 26
<212> TYPE: DNA
<213> ORGANISM: Artificial Sequence
<220> FEATURE:
<223> OTHER INFORMATION: Oligonucleotide

<400> SEQUENCE: 76
gctgtgaagc acctgcgttg ctcatg                                           26

<210> SEQ ID NO 77
<211> LENGTH: 30
<212> TYPE: DNA
<213> ORGANISM: Artificial Sequence
<220> FEATURE:
<223> OTHER INFORMATION: Oligonucleotide

<400> SEQUENCE: 77
gctgtgaaac acctgcattt acggccacgg                                       30

<210> SEQ ID NO 78
<211> LENGTH: 30
<212> TYPE: DNA
<213> ORGANISM: Artificial Sequence
<220> FEATURE:
<223> OTHER INFORMATION: Oligonucleotide

<400> SEQUENCE: 78
ccgtggccgt aaatgcaggt gtttcacagc                                       30

<210> SEQ ID NO 79
<211> LENGTH: 23
<212> TYPE: DNA
<213> ORGANISM: Artificial Sequence
```

```
<220> FEATURE:
<223> OTHER INFORMATION: Oligonucleotide

<400> SEQUENCE: 79
cctttcgcaa ttgactgaaa cac                                    23

<210> SEQ ID NO 80
<211> LENGTH: 19
<212> TYPE: DNA
<213> ORGANISM: Artificial Sequence
<220> FEATURE:
<223> OTHER INFORMATION: Oligonucleotide

<400> SEQUENCE: 80
ggctagaccg gggtgcgcg                                         19

<210> SEQ ID NO 81
<211> LENGTH: 24
<212> TYPE: DNA
<213> ORGANISM: Artificial Sequence
<220> FEATURE:
<223> OTHER INFORMATION: Oligonucleotide

<400> SEQUENCE: 81
aaggtggtta tttcacsctt agcg                                   24

<210> SEQ ID NO 82
<211> LENGTH: 21
<212> TYPE: DNA
<213> ORGANISM: Artificial Sequence
<220> FEATURE:
<223> OTHER INFORMATION: Oligonucleotide

<400> SEQUENCE: 82
gtcctctttg gggtaaatgt c                                      21

<210> SEQ ID NO 83
<211> LENGTH: 22
<212> TYPE: DNA
<213> ORGANISM: Artificial Sequence
<220> FEATURE:
<223> OTHER INFORMATION: Oligonucleotide

<400> SEQUENCE: 83
aatgctccgg tttcatgtca tc                                     22

<210> SEQ ID NO 84
<211> LENGTH: 20
<212> TYPE: DNA
<213> ORGANISM: Artificial Sequence
<220> FEATURE:
<223> OTHER INFORMATION: Oligonucleotide

<400> SEQUENCE: 84
tagttccttc tcacccggag                                        20

<210> SEQ ID NO 85
<211> LENGTH: 27
<212> TYPE: DNA
<213> ORGANISM: Artificial Sequence
<220> FEATURE:
<223> OTHER INFORMATION: Oligonucleotide

<400> SEQUENCE: 85
cacaagggcg ctttagtttg ttttccg                                27
```

```
<210> SEQ ID NO 86
<211> LENGTH: 28
<212> TYPE: DNA
<213> ORGANISM: Artificial Sequence
<220> FEATURE:
<223> OTHER INFORMATION: Oligonucleotide

<400> SEQUENCE: 86
atcccctgag agtttaattt tcgtcaag                                       28

<210> SEQ ID NO 87
<211> LENGTH: 23
<212> TYPE: DNA
<213> ORGANISM: Artificial Sequence
<220> FEATURE:
<223> OTHER INFORMATION: Oligonucleotide

<400> SEQUENCE: 87
taattcgtcg taattcgtcc tcc                                            23

<210> SEQ ID NO 88
<211> LENGTH: 24
<212> TYPE: DNA
<213> ORGANISM: Artificial Sequence
<220> FEATURE:
<223> OTHER INFORMATION: Oligonucleotide

<400> SEQUENCE: 88
ctctgccttc ctgttttttgt tgtg                                          24

<210> SEQ ID NO 89
<211> LENGTH: 30
<212> TYPE: DNA
<213> ORGANISM: Artificial Sequence
<220> FEATURE:
<223> OTHER INFORMATION: Oligonucleotide

<400> SEQUENCE: 89
aaacgcattt gcaactgtcg gcgcttttcc                                     30

<210> SEQ ID NO 90
<211> LENGTH: 29
<212> TYPE: DNA
<213> ORGANISM: Artificial Sequence
<220> FEATURE:
<223> OTHER INFORMATION: Oligonucleotide

<400> SEQUENCE: 90
cttgttacct caaaaaatca cagtgctcg                                      29

<210> SEQ ID NO 91
<211> LENGTH: 27
<212> TYPE: DNA
<213> ORGANISM: Artificial Sequence
<220> FEATURE:
<223> OTHER INFORMATION: Oligonucleotide

<400> SEQUENCE: 91
gcagtcggtg atgctggatt tgccctg                                        27

<210> SEQ ID NO 92
<211> LENGTH: 32
<212> TYPE: DNA
<213> ORGANISM: Artificial Sequence
<220> FEATURE:
<223> OTHER INFORMATION: Oligonucleotide
```

<400> SEQUENCE: 92
gtttttttac gggtaagccg caacgaccat tg                32

<210> SEQ ID NO 93
<211> LENGTH: 22
<212> TYPE: DNA
<213> ORGANISM: Artificial Sequence
<220> FEATURE:
<223> OTHER INFORMATION: Oligonucleotide

<400> SEQUENCE: 93
tagtagataa gttttagata ac                           22

<210> SEQ ID NO 94
<211> LENGTH: 25
<212> TYPE: DNA
<213> ORGANISM: Artificial Sequence
<220> FEATURE:
<223> OTHER INFORMATION: Oligonucleotide

<400> SEQUENCE: 94
taaaactgaa gttgccctga aaatg                        25

<210> SEQ ID NO 95
<211> LENGTH: 22
<212> TYPE: DNA
<213> ORGANISM: Artificial Sequence
<220> FEATURE:
<223> OTHER INFORMATION: Oligonucleotide

<400> SEQUENCE: 95
tgatgagtgg ttctgcaaga gg                           22

<210> SEQ ID NO 96
<211> LENGTH: 23
<212> TYPE: DNA
<213> ORGANISM: Artificial Sequence
<220> FEATURE:
<223> OTHER INFORMATION: Oligonucleotide

<400> SEQUENCE: 96
taaaagacag attacctggc ctg                          23

<210> SEQ ID NO 97
<211> LENGTH: 31
<212> TYPE: DNA
<213> ORGANISM: Artificial Sequence
<220> FEATURE:
<223> OTHER INFORMATION: Oligonucleotide

<400> SEQUENCE: 97
cggactacct caaaataaag ctttatatac g                 31

<210> SEQ ID NO 98
<211> LENGTH: 31
<212> TYPE: DNA
<213> ORGANISM: Artificial Sequence
<220> FEATURE:
<223> OTHER INFORMATION: Oligonucleotide

<400> SEQUENCE: 98
gtcatgatac cttgattaaa aaacaaacag c                 31

<210> SEQ ID NO 99

<211> LENGTH: 26
<212> TYPE: DNA
<213> ORGANISM: Artificial Sequence
<220> FEATURE:
<223> OTHER INFORMATION: Oligonucleotide

<400> SEQUENCE: 99
ggctataatg cgcacataac ctcttg                                            26

<210> SEQ ID NO 100
<211> LENGTH: 33
<212> TYPE: DNA
<213> ORGANISM: Artificial Sequence
<220> FEATURE:
<223> OTHER INFORMATION: Oligonucleotide

<400> SEQUENCE: 100
aatcttttct tattttttgg ctaacgaata gcc                                    33

<210> SEQ ID NO 101
<211> LENGTH: 31
<212> TYPE: DNA
<213> ORGANISM: Artificial Sequence
<220> FEATURE:
<223> OTHER INFORMATION: Oligonucleotide

<400> SEQUENCE: 101
gtccaacttt ttggggtcag tacaaacttt g                                      31

<210> SEQ ID NO 102
<211> LENGTH: 28
<212> TYPE: DNA
<213> ORGANISM: Artificial Sequence
<220> FEATURE:
<223> OTHER INFORMATION: Oligonucleotide

<400> SEQUENCE: 102
taataacgcc gttattaaat agcctgcc                                          28

<210> SEQ ID NO 103
<211> LENGTH: 26
<212> TYPE: DNA
<213> ORGANISM: Artificial Sequence
<220> FEATURE:
<223> OTHER INFORMATION: Oligonucleotide

<400> SEQUENCE: 103
taagcaacgt ctgcttactg cccctc                                            26

<210> SEQ ID NO 104
<211> LENGTH: 33
<212> TYPE: DNA
<213> ORGANISM: Artificial Sequence
<220> FEATURE:
<223> OTHER INFORMATION: Oligonucleotide

<400> SEQUENCE: 104
gtgatggctt ctgataaaga taaatttata gcc                                    33

<210> SEQ ID NO 105
<211> LENGTH: 18
<212> TYPE: DNA
<213> ORGANISM: Artificial Sequence
<220> FEATURE:
<223> OTHER INFORMATION: Oligonucleotide

<400> SEQUENCE: 105
taacaggcta agaggggc 18

<210> SEQ ID NO 106
<211> LENGTH: 28
<212> TYPE: DNA
<213> ORGANISM: Artificial Sequence
<220> FEATURE:
<223> OTHER INFORMATION: Oligonucleotide

<400> SEQUENCE: 106
attgccactc ttcttgatca aataaccg 28

<210> SEQ ID NO 107
<211> LENGTH: 29
<212> TYPE: DNA
<213> ORGANISM: Artificial Sequence
<220> FEATURE:
<223> OTHER INFORMATION: Oligonucleotide

<400> SEQUENCE: 107
aatgcgtctg ttgataattc aaattagtc 29

<210> SEQ ID NO 108
<211> LENGTH: 28
<212> TYPE: DNA
<213> ORGANISM: Artificial Sequence
<220> FEATURE:
<223> OTHER INFORMATION: Oligonucleotide

<400> SEQUENCE: 108
tagccgtttt attcagtata gatttgcg 28

<210> SEQ ID NO 109
<211> LENGTH: 23
<212> TYPE: DNA
<213> ORGANISM: Artificial Sequence
<220> FEATURE:
<223> OTHER INFORMATION: Oligonucleotide

<400> SEQUENCE: 109
gttcgtcggt aacccgtttc agc 23

<210> SEQ ID NO 110
<211> LENGTH: 20
<212> TYPE: DNA
<213> ORGANISM: Artificial Sequence
<220> FEATURE:
<223> OTHER INFORMATION: Oligonucleotide

<400> SEQUENCE: 110
atggcttaaa gagaggtgcc 20

<210> SEQ ID NO 111
<211> LENGTH: 22
<212> TYPE: DNA
<213> ORGANISM: Artificial Sequence
<220> FEATURE:
<223> OTHER INFORMATION: Oligonucleotide

<400> SEQUENCE: 111
cgtactttaa agggagaatg ac 22

<210> SEQ ID NO 112
<211> LENGTH: 22
<212> TYPE: DNA

```
<213> ORGANISM: Artificial Sequence
<220> FEATURE:
<223> OTHER INFORMATION: Oligonucleotide

<400> SEQUENCE: 112
gtgcttcctc attatggtga cg                                       22

<210> SEQ ID NO 113
<211> LENGTH: 20
<212> TYPE: DNA
<213> ORGANISM: Artificial Sequence
<220> FEATURE:
<223> OTHER INFORMATION: Oligonucleotide

<400> SEQUENCE: 113
gaatggaggg agattacacg                                          20

<210> SEQ ID NO 114
<211> LENGTH: 21
<212> TYPE: DNA
<213> ORGANISM: Artificial Sequence
<220> FEATURE:
<223> OTHER INFORMATION: Oligonucleotide

<400> SEQUENCE: 114
ccttagtggg taaacgctta c                                        21

<210> SEQ ID NO 115
<211> LENGTH: 21
<212> TYPE: DNA
<213> ORGANISM: Artificial Sequence
<220> FEATURE:
<223> OTHER INFORMATION: Oligonucleotide

<400> SEQUENCE: 115
ctttcaggca gctaaggaaa g                                        21

<210> SEQ ID NO 116
<211> LENGTH: 29
<212> TYPE: DNA
<213> ORGANISM: Artificial Sequence
<220> FEATURE:
<223> OTHER INFORMATION: Oligonucleotide

<400> SEQUENCE: 116
caatatgtat tattgattga gtaaacggg                                29

<210> SEQ ID NO 117
<211> LENGTH: 20
<212> TYPE: DNA
<213> ORGANISM: Artificial Sequence
<220> FEATURE:
<223> OTHER INFORMATION: Oligonucleotide

<400> SEQUENCE: 117
cctcttccag gaataatccc                                          20

<210> SEQ ID NO 118
<211> LENGTH: 20
<212> TYPE: DNA
<213> ORGANISM: Artificial Sequence
<220> FEATURE:
<223> OTHER INFORMATION: Oligonucleotide

<400> SEQUENCE: 118
cggaaagcgg ttcacagatc                                          20
```

<210> SEQ ID NO 119
<211> LENGTH: 23
<212> TYPE: DNA
<213> ORGANISM: Artificial Sequence
<220> FEATURE:
<223> OTHER INFORMATION: Oligonucleotide

<400> SEQUENCE: 119
ctcgtaagtt tcgcagctta tta                                    23

<210> SEQ ID NO 120
<211> LENGTH: 20
<212> TYPE: DNA
<213> ORGANISM: Artificial Sequence
<220> FEATURE:
<223> OTHER INFORMATION: Oligonucleotide

<400> SEQUENCE: 120
tgaaattcct gtccgacagg                                        20

<210> SEQ ID NO 121
<211> LENGTH: 21
<212> TYPE: DNA
<213> ORGANISM: Artificial Sequence
<220> FEATURE:
<223> OTHER INFORMATION: Oligonucleotide

<400> SEQUENCE: 121
gcactaccgc aatgttattg c                                      21

<210> SEQ ID NO 122
<211> LENGTH: 24
<212> TYPE: DNA
<213> ORGANISM: Artificial Sequence
<220> FEATURE:
<223> OTHER INFORMATION: Oligonucleotide

<400> SEQUENCE: 122
gcttacccaa taaatagtta cacg                                   24

<210> SEQ ID NO 123
<211> LENGTH: 23
<212> TYPE: DNA
<213> ORGANISM: Artificial Sequence
<220> FEATURE:
<223> OTHER INFORMATION: Oligonucleotide

<400> SEQUENCE: 123
taaaacctgt cacaaatcac aaa                                    23

<210> SEQ ID NO 124
<211> LENGTH: 21
<212> TYPE: DNA
<213> ORGANISM: Artificial Sequence
<220> FEATURE:
<223> OTHER INFORMATION: Oligonucleotide

<400> SEQUENCE: 124
gtggcctgct tcaaactttc g                                      21

<210> SEQ ID NO 125
<211> LENGTH: 23
<212> TYPE: DNA
<213> ORGANISM: Artificial Sequence
<220> FEATURE:

<223> OTHER INFORMATION: Oligonucleotide

<400> SEQUENCE: 125
gtaaagtcta gcctggcggt tcg                                        23

<210> SEQ ID NO 126
<211> LENGTH: 31
<212> TYPE: DNA
<213> ORGANISM: Artificial Sequence
<220> FEATURE:
<223> OTHER INFORMATION: Oligonucleotide

<400> SEQUENCE: 126
taattctggt acgcctggca gatattttgc c                               31

<210> SEQ ID NO 127
<211> LENGTH: 24
<212> TYPE: DNA
<213> ORGANISM: Artificial Sequence
<220> FEATURE:
<223> OTHER INFORMATION: Oligonucleotide

<400> SEQUENCE: 127
atcaacctca aagggaaat cggg                                        24

<210> SEQ ID NO 128
<211> LENGTH: 23
<212> TYPE: DNA
<213> ORGANISM: Artificial Sequence
<220> FEATURE:
<223> OTHER INFORMATION: Oligonucleotide

<400> SEQUENCE: 128
taacttgttg taagccggat cgg                                        23

<210> SEQ ID NO 129
<211> LENGTH: 23
<212> TYPE: DNA
<213> ORGANISM: Artificial Sequence
<220> FEATURE:
<223> OTHER INFORMATION: Oligonucleotide

<400> SEQUENCE: 129
tgaagcatct atcgccggtt gcg                                        23

<210> SEQ ID NO 130
<211> LENGTH: 28
<212> TYPE: DNA
<213> ORGANISM: Artificial Sequence
<220> FEATURE:
<223> OTHER INFORMATION: Oligonucleotide

<400> SEQUENCE: 130
gattagaaat cctttttgaaa gcgcattg                                  28

<210> SEQ ID NO 131
<211> LENGTH: 20
<212> TYPE: DNA
<213> ORGANISM: Artificial Sequence
<220> FEATURE:
<223> OTHER INFORMATION: Oligonucleotide

<400> SEQUENCE: 131
cttattgggc accgcaatgg                                            20

```
<210> SEQ ID NO 132
<211> LENGTH: 27
<212> TYPE: DNA
<213> ORGANISM: Artificial Sequence
<220> FEATURE:
<223> OTHER INFORMATION: Oligonucleotide

<400> SEQUENCE: 132
cgaacacaat aaagatttaa ttcagcc                                27

<210> SEQ ID NO 133
<211> LENGTH: 20
<212> TYPE: DNA
<213> ORGANISM: Artificial Sequence
<220> FEATURE:
<223> OTHER INFORMATION: Oligonucleotide

<400> SEQUENCE: 133
ctgatgctac tgtgtcaacg                                        20

<210> SEQ ID NO 134
<211> LENGTH: 22
<212> TYPE: DNA
<213> ORGANISM: Artificial Sequence
<220> FEATURE:
<223> OTHER INFORMATION: Oligonucleotide

<400> SEQUENCE: 134
aataatcaga catagcttag gc                                     22

<210> SEQ ID NO 135
<211> LENGTH: 21
<212> TYPE: DNA
<213> ORGANISM: Artificial Sequence
<220> FEATURE:
<223> OTHER INFORMATION: Oligonucleotide

<400> SEQUENCE: 135
gccgtgatgg ttttcgcgtt c                                      21

<210> SEQ ID NO 136
<211> LENGTH: 21
<212> TYPE: DNA
<213> ORGANISM: Artificial Sequence
<220> FEATURE:
<223> OTHER INFORMATION: Oligonucleotide

<400> SEQUENCE: 136
tattttcctc ccgcgctaaa g                                      21

<210> SEQ ID NO 137
<211> LENGTH: 23
<212> TYPE: DNA
<213> ORGANISM: Artificial Sequence
<220> FEATURE:
<223> OTHER INFORMATION: Oligonucleotide

<400> SEQUENCE: 137
ttcagctgat gaccaccacg ctt                                    23

<210> SEQ ID NO 138
<211> LENGTH: 23
<212> TYPE: DNA
<213> ORGANISM: Artificial Sequence
<220> FEATURE:
<223> OTHER INFORMATION: Oligonucleotide
```

-continued

```
<400> SEQUENCE: 138
gagttgtcag agcaggatga ttc                                      23

<210> SEQ ID NO 139
<211> LENGTH: 22
<212> TYPE: DNA
<213> ORGANISM: Artificial Sequence
<220> FEATURE:
<223> OTHER INFORMATION: Oligonucleotide

<400> SEQUENCE: 139
tatctgcgct tatcctttat gg                                       22

<210> SEQ ID NO 140
<211> LENGTH: 23
<212> TYPE: DNA
<213> ORGANISM: Artificial Sequence
<220> FEATURE:
<223> OTHER INFORMATION: Oligonucleotide

<400> SEQUENCE: 140
cctttacggt gataaccgtc gcg                                      23

<210> SEQ ID NO 141
<211> LENGTH: 25
<212> TYPE: DNA
<213> ORGANISM: Artificial Sequence
<220> FEATURE:
<223> OTHER INFORMATION: Oligonucleotide

<400> SEQUENCE: 141
ctgacaagcc tctcattctc ttgtc                                    25

<210> SEQ ID NO 142
<211> LENGTH: 23
<212> TYPE: DNA
<213> ORGANISM: Artificial Sequence
<220> FEATURE:
<223> OTHER INFORMATION: Oligonucleotide

<400> SEQUENCE: 142
gagaattatc gaggtccggt atc                                      23

<210> SEQ ID NO 143
<211> LENGTH: 22
<212> TYPE: DNA
<213> ORGANISM: Artificial Sequence
<220> FEATURE:
<223> OTHER INFORMATION: Oligonucleotide

<400> SEQUENCE: 143
ctacgcgtta gcgatagact gc                                       22

<210> SEQ ID NO 144
<211> LENGTH: 31
<212> TYPE: DNA
<213> ORGANISM: Artificial Sequence
<220> FEATURE:
<223> OTHER INFORMATION: Oligonucleotide

<400> SEQUENCE: 144
aggcttacta agaacaccag ggggagggga a                             31

<210> SEQ ID NO 145
<211> LENGTH: 30
```

-continued

```
<212> TYPE: DNA
<213> ORGANISM: Artificial Sequence
<220> FEATURE:
<223> OTHER INFORMATION: Oligonucleotide

<400> SEQUENCE: 145
agtcataagc ttccccgctt actaagacta                                    30

<210> SEQ ID NO 146
<211> LENGTH: 22
<212> TYPE: DNA
<213> ORGANISM: Artificial Sequence
<220> FEATURE:
<223> OTHER INFORMATION: Oligonucleotide

<400> SEQUENCE: 146
cctcaaatcg gccataataa cc                                            22

<210> SEQ ID NO 147
<211> LENGTH: 22
<212> TYPE: DNA
<213> ORGANISM: Artificial Sequence
<220> FEATURE:
<223> OTHER INFORMATION: Oligonucleotide

<400> SEQUENCE: 147
taaacaccgt cgtcagaaat gc                                            22

<210> SEQ ID NO 148
<211> LENGTH: 25
<212> TYPE: DNA
<213> ORGANISM: Artificial Sequence
<220> FEATURE:
<223> OTHER INFORMATION: Oligonucleotide

<400> SEQUENCE: 148
tagactttta tccactttat tgctg                                         25

<210> SEQ ID NO 149
<211> LENGTH: 25
<212> TYPE: DNA
<213> ORGANISM: Artificial Sequence
<220> FEATURE:
<223> OTHER INFORMATION: Oligonucleotide

<400> SEQUENCE: 149
gtgtgccttt cggcgatatg gcgtg                                         25

<210> SEQ ID NO 150
<211> LENGTH: 25
<212> TYPE: DNA
<213> ORGANISM: Artificial Sequence
<220> FEATURE:
<223> OTHER INFORMATION: Oligonucleotide

<400> SEQUENCE: 150
cctttacgtg ggcggtgatt ttgtc                                         25

<210> SEQ ID NO 151
<211> LENGTH: 24
<212> TYPE: DNA
<213> ORGANISM: Artificial Sequence
<220> FEATURE:
<223> OTHER INFORMATION: Oligonucleotide

<400> SEQUENCE: 151
```

| | |
|---|---|
| tagctttgct cctggatgtt tgcc | 24 |

<210> SEQ ID NO 152
<211> LENGTH: 30
<212> TYPE: DNA
<213> ORGANISM: Artificial Sequence
<220> FEATURE:
<223> OTHER INFORMATION: Oligonucleotide

<400> SEQUENCE: 152

| | |
|---|---|
| gctgtaattt attcagcgtt tgtacatacg | 30 |

<210> SEQ ID NO 153
<211> LENGTH: 26
<212> TYPE: DNA
<213> ORGANISM: Artificial Sequence
<220> FEATURE:
<223> OTHER INFORMATION: Oligonucleotide

<400> SEQUENCE: 153

| | |
|---|---|
| tcagtcaact cgctgcggcg tgttac | 26 |

<210> SEQ ID NO 154
<211> LENGTH: 28
<212> TYPE: DNA
<213> ORGANISM: Artificial Sequence
<220> FEATURE:
<223> OTHER INFORMATION: Oligonucleotide

<400> SEQUENCE: 154

| | |
|---|---|
| cttattgttg cttagttagg gtagtcac | 28 |

<210> SEQ ID NO 155
<211> LENGTH: 26
<212> TYPE: DNA
<213> ORGANISM: Artificial Sequence
<220> FEATURE:
<223> OTHER INFORMATION: Oligonucleotide

<400> SEQUENCE: 155

| | |
|---|---|
| cagtcagtct caggggagga gcaatc | 26 |

<210> SEQ ID NO 156
<211> LENGTH: 30
<212> TYPE: DNA
<213> ORGANISM: Artificial Sequence
<220> FEATURE:
<223> OTHER INFORMATION: Oligonucleotide

<400> SEQUENCE: 156

| | |
|---|---|
| tgaatgcaca ataaaaaaat cccgaccctg | 30 |

<210> SEQ ID NO 157
<211> LENGTH: 25
<212> TYPE: DNA
<213> ORGANISM: Artificial Sequence
<220> FEATURE:
<223> OTHER INFORMATION: Oligonucleotide

<400> SEQUENCE: 157

| | |
|---|---|
| agtcgcgcag tactcctctt accag | 25 |

<210> SEQ ID NO 158
<211> LENGTH: 24
<212> TYPE: DNA
<213> ORGANISM: Artificial Sequence

```
<220> FEATURE:
<223> OTHER INFORMATION: Oligonucleotide

<400> SEQUENCE: 158
taatttctca tcaggcggct ctgc                                              24

<210> SEQ ID NO 159
<211> LENGTH: 24
<212> TYPE: DNA
<213> ORGANISM: Artificial Sequence
<220> FEATURE:
<223> OTHER INFORMATION: Oligonucleotide

<400> SEQUENCE: 159
taacattatc agcctgctga cggc                                              24

<210> SEQ ID NO 160
<211> LENGTH: 28
<212> TYPE: DNA
<213> ORGANISM: Artificial Sequence
<220> FEATURE:
<223> OTHER INFORMATION: Oligonucleotide

<400> SEQUENCE: 160
ggccgaattc gtagggtaca gaggtaag                                          28

<210> SEQ ID NO 161
<211> LENGTH: 30
<212> TYPE: DNA
<213> ORGANISM: Artificial Sequence
<220> FEATURE:
<223> OTHER INFORMATION: Oligonucleotide

<400> SEQUENCE: 161
ggccggatcc gtcattactg actggggcgg                                        30
```

IDENTIFICATION OF NEW SMALL RNAS AND ORFS OF *E. COLI* AS MEDIATORS OF CELL AND INTERCELL REGULATION

RELATED APPLICATIONS

This application is a continuation and claims the benefit of priority of International Application No. PCT/US02/03147 filed Jan. 31, 2002, designating the United States of America and published in English, which claims the benefit of priority of U.S. Provisional Application No. 60/266,402 filed Feb. 1, 2001, both of which are hereby expressly incorporated by reference in their entireties.

FIELD OF THE INVENTION

The invention relates to new small RNAs and ORFs of *E. coli* as mediators of cell and intercell regulation.

BACKGROUND OF THE INVENTION

In the last few years, the importance of regulatory small RNAs (sRNAs) as mediators of a number of cellular processes in bacteria has begun to be recognized. Although instances of naturally occurring antisense RNAs have been known for many years, the participation of sRNAs in protein tagging for degradation, modulation of RNA polymerase activity, and stimulation of translation are relatively recent discoveries (see Wassarman, K. M. et al. 1999 *Trends Microbiol* 7:37–45 for review; Wassarman, K. M. and Storz, G. 2000 *Cell* 101:613–623). These findings have raised questions about how extensively sRNAs are used, what other cellular activities might be regulated by sRNAs, and what other mechanisms of action exist for sRNAs. In addition, prokaryotic sRNAs appear to target different cellular functions than their eukaryotic counterparts that primarily act during RNA biogenesis. It is unclear whether this difference between prokaryotic and eukaryotic sRNAs is accurate or stems from the incompleteness of current knowledge. Implicit in these questions is the question of how many sRNAs exist in a given organism and whether the current known sRNAs are truly representative of sRNA function in general.

To date, most known bacterial sRNAs have been identified fortuitously by the direct detection of highly abundant sRNAs (4.5S RNA, tmRNA, 6S RNA, RNase P RNA, and Spot42 RNA), by the observation of an sRNA during studies on proteins (OxyS RNA, Crp Tic RNA, CsrB RNA, and GcvB RNA) or by the discovery of activities associated with overexpression of genomic fragments (MicF RNA, DicF RNA, DsrA RNA, and RprA RNA) (Okamoto, K. and Freundlich, M. 1986 *PNAS USA* 83:5000–5004; Bhasin, R. S. 1989 Studies on the mechanism of the autoregulation of the crp operon of *E. coli* K12 In: Dept. of Biochemistry and Cell Biology, State University of New York at Stonybrook; Urbanowski, M. L. et al. 2000 *Mol Microbiol* 37:856–868; Wassarman, K. M. and Storz, G. 2000 *Cell* 101:613–623; Majdalani, N. et al. 2001 *Mol Microbiol* 39:1382–1394; for review see Wassarman, K. M. et al. 1999 *Trends Microbiol* 7:37–45). None of the *E. coli* sRNAs were found as a result of mutational screens. This observation may reflect the small target size of genes encoding sRNAs compared to protein genes, or may be a consequence of the regulatory rather than essential nature of many sRNA functions. The complete genome sequence of an organism provides a rapid inventory of most encoded proteins, tRNAs, and rRNAs, but it has not led to the immediate recognition of other genes that are not translated. In particular, new bacterial sRNA genes have been overlooked, as there are no identifiable classes of sRNAs that can be found based solely on sequence determinants.

SEGUE TO THE SUMMARY OF THE INVENTION

We and others have previously suggested several approaches to look for new sRNAs including computer searching of complete genomes based on parameters common to sRNAs, probing of genomic microarrays, and isolating sRNAs based on an association with general RNA binding proteins (Wassarman, K. M. et al. 1999 *Trends Microbiol* 7:37–45; Eddy, S. R. 1999 *Curr Opin Genet Dev* 9:695–699). Using a combination of these approaches, we have identified 17 novel sRNAs; in addition, we have found six small transcripts that contain short conserved open reading frames (ORFs).

SUMMARY OF THE INVENTION

A burgeoning list of small RNAs with a variety of regulatory functions has been identified in both prokaryotic and eukaryotic cells. However, it remains difficult to identify small RNAs by sequence inspection. We utilized the high conservation of small RNAs among closely related bacterial species, as well as analysis of transcripts detected by high-density oligonucleotide probe arrays, to predict the presence of novel small RNA genes in the intergenic regions of the *Escherichia coli* genome. The existence of 23 distinct new RNA species was confirmed by Northern analysis. Of these, six are predicted to encode short ORFs, whereas 17 are novel functional small RNAs. Based on the interaction of these small RNAs with the RNA binding protein Hfq, the modulation of rpoS expression, and other information, we contemplate these new small RNAs and ORFs of *E. coli* as mediators of cell and intercell regulation. As such, we anticipate their use in the development of diagnostics and in the development of antibiotics.

BRIEF DESCRIPTION OF THE DRAWINGS

FIG. 4 shows results of coimmunoprecipitation of sRNAs with the Hfq protein. (A) Immunoprecipitations using extract from MG1655 cells grown in LB medium in exponential growth ($OD_{600}$=0.4) were done using no antibody (lane 1); 5 μl of preimmune serum (lane 2); or 0.5, 1, 5, or 10 μl of hfq antisera (lanes 3–6). Selected RNAs were fractionated on a 10% polyacrylamide urea gel after 3'-end labeling. Asterisks mark RNA bands present in the anti-hfq precipitated samples but not in the preimmune control samples and therefore represent Hfq-interacting RNAs. (B) Immunoprecipitations were done using extract from MG1655 cells grown under three different growth conditions: (E) exponential growth in LB medium; (M) exponential growth in M63-glucose medium, and (S) stationary phase in LB medium. Immunoprecipitations were carried out with 5 μl of preimmune sera (lane 1) or 5 μl Hfq antisera (lane 2) and compared to total RNA from 1/10 extract equivalent used in the immunoprecipitations (lane 3). RNAs were fractionated on 10% polyacrylamide urea gels and analyzed by Northern hybridization using RNA probes to previously known sRNAs or our novel RNAs as indicated.

Brief Description of the Sequences

Figure 1A:
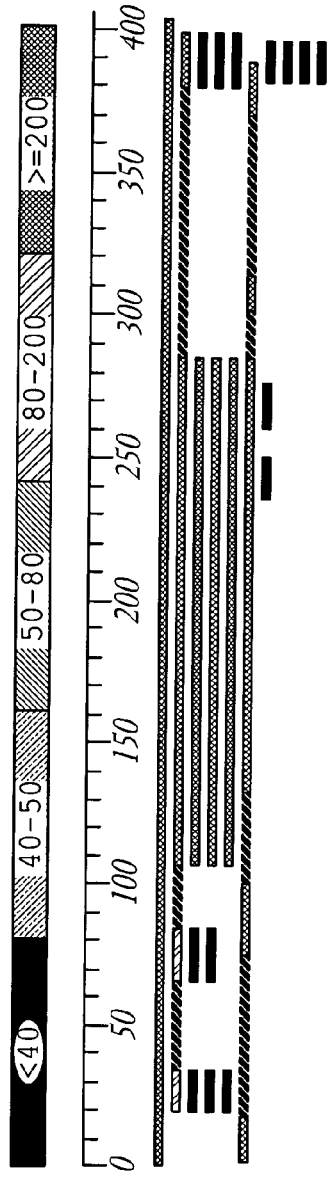
FIG. 1 shows BLAST alignments of representative Ig regions. The indicated Ig regions were used in a BLAST search of the NCBI Unfinished Microbial Genomes database. Each panel shows the summary figure provided by the BLAST program for matches to *Salmonella enteritidis, Salmonella paratyphi* A, *Salmonella typhi, Salmonella typhimurium* LT2 and *Klebsiella pneumoniae*, three contain known sRNA genes (rprA, csrB, and oxyS), and four contain sRNA candidates (#14, #17, #52, and #36; see Table 1). For each panel, the center numbered line represents the length of the full Ig region; the orientation of flanking genes is given by >(clockwise) or <(counterclockwise). The top hatched line in each panel is the match to *E. coli* (full identity throughout the Ig). The other hatched or double-diagonal lines resulted from the closest matches, and the other lines indicate additional less homologous matches. Location of the conserved region with respect to the borders of the Ig region also was a criterion used for the selection of our candidates; conservation 3' to an ORF or far from the 5' start of an ORF was considered more likely to encode an sRNA. Note that the conservation within the Ig region encoding oxyS might be interpreted as a leader sequence based on location relative to the start of the flanking gene (oxyR). However, the conservation extends for 185 nt, and therefore candidate regions in our search in which the conservation was near the start of an ORF but was longer than 150 nt were considered further.

| Candidate Number | SEQ ID NO |
|---|---|
| 12 | 1 |
| 14 | 2 |
| 22 | 3 |
| 24 | 4 |
| 25 | 5 |
| 26 | 6 |
| 27 | 7 |
| 31 | 8 |
| 38 | 9 |
| 40 | 10 |
| 41-I | 11 |
| 41-II | 12 |
| 52-I | 13 |
| 52-II | 14 |
| 55-I | 15 |
| 55-II | 16 |
| 61 | 17 |
| 8 | 18 |
| 43 | 19 |
| 9 (nucleotide) | 20 |
| 9 (amino acid) | 21 |
| 17 (nucleotide) | 22 |
| 17 (amino acid) | 23 |
| 28 (nucleotide) | 24 |
| 28 (amino acid) | 25 |
| 36 (nucleotide) | 26 |
| 36 (amino acid) | 27 |
| 49 (nucleotide) | 28 |
| 49 (amino acid) | 29 |
| 50 (nucleotide) | 30 |
| 50 (amino acid) | 31 |

DETAILED DESCRIPTION OF THE PREFERRED EMBODIMENT

By "RNA" or "gene product" or "transcription product" is meant the RNA encoded by the E. coli gene or RNA substantially homologous or complementary thereto or a derivative or fragment thereof having RNA activity. Encompassed by the definition of "RNA" are variants of RNA in which there have been trivial mutations such as substitutions, deletions, insertions or other modifications of the native RNA. The term "substantial homology" or "substantial identity", when referring to polypeptides or polynucleotides, indicates that the sequence of a polypeptide or polynucleotide in question, when properly aligned, exhibits at least about 30% identity with the sequence of an entire naturally occurring polypeptide or polynucleotide or a portion thereof. Polynucleotides of the present invention which are homologous or substantially homologous to, for example, the polynucleotides of the invention are usually at least about 70% identity to that shown in the Sequence Listing, preferably at least about 90% identity and most preferably at least about 95% identity, or a complement thereof. Any technique known in the art can be used to sequence polynucleotides, including, for example, dideoxynucleotide sequencing (Sanger et al. 1977 PNAS USA 74:5463–5467), or using the Sequenase™ kit (United States Biochemical Corp.). Homologs of polynucleotides and polypeptides, whether synthetically or recombinantly produced or found in nature, are also encompassed by the scope of the invention, and are herein defined as polynucleotides and polypeptides which are homologous to, respectively, polynucleotides and polypeptides of the invention, or fragments, variants, or complements thereof. Homologous polynucleotides and polypeptides are generally encoded by homologous genes as described above, and retain significant amino acid residue or nucleotide identity to the genes of the invention. Such polypeptides can be expressed by other organisms such as bacteria, yeast and higher order organisms such as mammals. Various methods of determining amino acid residue or nucleotide identity are known in the art. Homologous polynucleotides or polypeptides can be obtained by in vitro synthesis by expressing genes derived from other bacteria or by mutagenizing genes of the invention. Also included in the definition of "substantially homologous polynucleotides" would be those polynucleotides which, when annealed under conditions known in the art, would remain annealed under moderate wash conditions also known in the art (such as washing in 6×SSPE twice at room temperature and then twice at 37° C.) (Wahl et al. 1987 *Methods in Enzymology* 152 Academic Press Inc., San Diego).

Polynucleotide and polypeptide homology is typically measured using sequence analysis software. See, e.g., Sequence Analysis Software Package of the Genetics Computer Group, University of Wisconsin Biotechnology Center, 1710 University Avenue, Madison, Wis. 53705.

By "polynucleotide" or "nucleic acid" is meant a single- or double-stranded DNA, genomic DNA, cDNA, RNA, DNA-RNA hybrid, or a polymer comprising purine and pyrimidine bases, or other natural, chemically or biochemically modified or containing non-natural or derivatized nucleotide bases. The backbone of the polynucleotide can comprise sugars and phosphate groups (as typically found in RNA or DNA), or modified or substituted sugar or phosphate groups. Alternatively, the backbone of the polynucleotide can comprise a polymer of synthetic subunits such as phosphoramidates and is thus a oligodeoxynucleoside phosphoramidate ($P-NH_2$) or a mixed phosphoramidate-phosphodiester oligomer (Peyrottes et al. 1996 *Nucleic Acids Res* 24:1841–8; Chaturvedi et al. 1996 *Nucleic Acids Res* 24:2318–23; and Schultz et al. 1996 *Nucleic Acids Res* 24:2966–73). In another embodiment, a phosphorothiate linkage can be used in place of a phosphodiester linkage (Braun et al. 1988 *J Immunol* 141:2084–9; and Latimer et al. 1995 *Mol Immunol* 32:1057–1064). In addition, a double-stranded polynucleotide can be obtained from the single-stranded polynucleotide product of chemical synthesis either by synthesizing the complementary strand and annealing the strands under appropriate conditions, or by synthesizing the complementary strand de novo using a DNA polymerase with an appropriate primer.

A nucleic acid is said to "encode" an RNA or a polypeptide if, in its native state or when manipulated by methods known to those skilled in the art, it can be transcribed and/or translated to produce the RNA, the polypeptide or a fragment thereof. The anti-sense strand of such a nucleic acid is also said to encode the sequence. The polynucleotides of the present invention comprise those which are naturally-occurring, synthetic or recombinant.

A "recombinant" nucleic acid is one which is chemically synthesized or the product of the artificial manipulation of isolated segments of nucleic acids, e.g., by genetic engineering techniques. Isolated segments within a recombinant nucleic acid can be naturally occurring sequences.

By "polynucleotide" or "gene" or "RNA" and the like is meant a polynucleotide encoding or comprising the RNA of the invention, or a homolog, fragment, derivative or complement thereof and having RNA activity as described herein. As is known in the art, a DNA can be transcribed by an RNA polymerase to produce RNA, but an RNA can be reverse transcribed by reverse transcriptase to produce a DNA. Thus a DNA can encode an RNA and vice versa.

The invention also encompasses vectors such as single- and double-stranded plasmids or viral vectors comprising RNA, DNA or a mixture or variant thereof, further comprising a polynucleotide of the invention. A wide variety of suitable expression systems are known in the art and are selected based on the host cells used, inducibility of expression desired and ease of use. The non-transcribed portions of a gene and the non-coding portions of a gene can be modified as known in the art. For example, the native promoters can be deleted, substituted or supplemented with other promoters known in the art; transcriptional enhancers, inducible promoters or other transcriptional control elements can be added, as can be replication origins and replication initiator proteins, autonomously replicating sequence (ARS), marker genes (e.g. antibiotic resistance markers), sequences for chromosomal integration (e.g., viral integration sites or sequences homologous to chromosomal sequences), restriction sites, multiple cloning sites, ribosome-binding sites, RNA splice sites, polyadenylation sites, transcriptional terminator sequences, mRNA stabilizing sequences, 5' stem-loop to protect against degradation, and other elements commonly found on plasmids and other vectors known in the art. Secretion signals from secreted polypeptides can also be included to allow the polypeptide to cross and/or lodge in cell membranes or be secreted from the cell. Such vectors can be prepared by means of standard recombinant techniques discussed, for example, in Sambrook et al. 1989 *Molecular Cloning: A Laboratory Manual*, 2nd edition, Cold Spring Harbor Press, Cold Spring Harbor Laboratory, N.Y.; and Ausubel et al. (eds.), 1987 *Current Protocols in Molecular Biology*, Greene Publishing Associates, Brooklyn, N.Y.). Many useful vectors are known in the art and can be obtained from vendors including, but not limited to, Stratagene, New England Biolabs, and Promega Biotech.

An appropriate promoter and other necessary vector sequences are selected so as to be functional in the chosen host. While prokaryotic host cells are preferred, mammalian or other eukaryotic host cells, including, but not limited to, yeast, filamentous fungi, plant, insect, amphibian or avian species, can also be useful for production of the polypeptides of the present invention. See, Kruse et al. (eds.) 1973 *Tissue Culture* Academic Press. Examples of workable combinations of cell lines and expression vectors are described in Sambrook et al. 1989 or Ausubel et al. 1987; see also, e.g., Metzger et al. 1988 *Nature* 334:31–36. Examples of commonly used mammalian host cell lines are VERO and HeLa cells, Chinese hamster ovary (CHO) cells, and W138, BHK, and COS cell lines, or others as appropriate, e.g., to provide higher expression, desirable glycosylation patterns, etc.

By "bacterial host cell" or "bacteria" or "bacterium" is meant various micro-organism(s) containing at least one chromosome but lacking a discrete nuclear membrane. Representatives include *E. coli, Bacillus, Salmonella, Pseudomonas, Staphylococcus* and other *eubacteria, archaebacteria, chlamydia* and *rickettsia* and related organisms, and the like, and may be spherical, rod-like, straight, curved, spiral, filamentous or other shapes.

Vectors suitable for use with various cells can comprise promoters which can, when appropriate, include those naturally associated with genes of the invention. Promoters can be operably linked to a polynucleotide of the invention.

A nucleic acid sequence is "operably linked" when it is placed into a functional relationship with another nucleic acid sequence. For instance, a promoter is operably linked to a coding sequence if the promoter affects the transcription or expression of the gene. Generally, operably linked means that the DNA sequences being linked are contiguous and, where necessary to join two protein coding regions, contiguous and in reading frame.

Promoters can be inducible or repressible by factors which respond biochemically to changes in temperature, osmolarity, carbon source, sugars, etc., as is known in the art. Promoters including, but not limited to, the trp, lac and phage promoters, tRNA promoters and glycolytic enzyme promoters can be used in prokaryotic hosts. Useful yeast promoters include, but are not limited to, the promoter regions for metallothionein, 3-phosphoglycerate kinase or other glycolytic enzymes such as enolase or glyceraldehyde-3-phosphate dehydrogenase, enzymes responsible for maltose and galactose utilization. Appropriate foreign mammalian promoters include, but are not limited to, the early and late promoters from SV40 (Fiers et al. 1978 *Nature* 273: 113–120) and promoters derived from murine Moloney leukemia virus, mouse mammary tumor virus, avian sarcoma viruses, adenovirus II, bovine papilloma virus or polyoma. In addition, the construct can be joined to an amplifiable gene (e.g., DHFR) so that multiple copies of the construct can be made. For appropriate enhancer and other expression control sequences suitable for vectors, see also *Enhancers and Eukaryotic Gene Expression*, Cold Spring Harbor Press: N.Y. 1983.

While expression vectors are preferably autonomously replicating, they can also be inserted into the genome of the host cell by methods known in the art. Expression and cloning vectors preferably contain a selectable marker which is a gene encoding a protein necessary under at least one control for the survival or growth of a host cell transformed with the vector. The presence of this gene ensures the growth of only those host cells which express the inserts. Typical selection genes are known in the art and include, but are not limited to, those which encode proteins that (a) confer resistance to antibiotics or other toxic substances, e.g., ampicillin, neomycin, methotrexate, etc.; (b) complement auxotrophic deficiencies, or (c) supply critical nutrients not available from complex media, e.g., the gene encoding D-alanine racemase for Bacilli. The choice of the proper selectable marker depends on the host cell, as appropriate markers for different hosts are well known.

As one of skill in the art will understand, the choice in construction and arrangement of markers, promoters, origins of replication, etc. in various vectors of the present invention will be dictated by the desired level and timing of expression of RNA of the invention, with the ultimate goal of regulating the production of metabolic compounds in the host cell.

By "protein" or "polypeptide" is meant a polypeptide encoded by the *E. coli* gene of the invention or a polypeptide substantially homologous thereto and having protein activity. Encompassed by the proteins of the invention are variants thereof in which there have been trivial substitutions, deletions, insertions or other modifications of the native polypeptide which substantially retain protein characteristics, particularly silent or conservative substitutions. Silent nucleotide substitutions are changes of one or more nucleotides which do not change any amino acid of protein. Conservative substitutions include substitutions within the following groups: glycine, alanine; valine, isoleucine, leucine; aspartic acid, glutamic acid; asparagine, glutamine; serine, threonine; lysine, arginine; and phenylalanine, tyrosine. Such conservative substitutions are not expected to interfere with biochemical activity, particularly when they occur in structural regions (e.g., alpha helices or beta pleated sheets) of the polypeptide, which can be predicted by standard computer analysis of the amino acid sequence of the protein. Also encompassed by the claimed polypeptides of the invention are polypeptides encoded by polynucleotides which are substantially homologous to a polynucleotide of the invention.

Nucleic acids encoding the polypeptides of the present invention include not only native or wild-type sequences but also any sequence capable of encoding the polypeptide, which can be synthesized by making use of the redundancy in the genetic code. Various codon substitutions can be introduced, e.g., silent or conservative changes as discussed above. Due to degeneracy in the genetic code there is some degree of flexibility in the third base of each codon and some amino acid residues are encoded by several different codons. Each possible codon could be used in the gene to encode the protein. While this may appear to present innumerable choices, in practice, each host has a particular preferred codon usage, so that genes can be tailored for optimal translation in the host in which they are expressed. Thus, synthetic genes that encode the proteins of the invention are included in this invention.

Techniques for nucleic acid manipulation are described generally, for example, in Sambrook et al. (1989) and Ausubel et al. (1987). Reagents useful in applying such techniques, such as restriction enzymes and the like, are widely known in the art and commercially available from vendors including, but not limited to, New England BioLabs, Boehringer Mannheim, Amersham, Promega Biotech, U.S. Biochemicals, New England Nuclear, and a number of other sources.

Nucleic acid probes and primers based on sequences of the invention can be prepared by standard techniques. Such a probe or primer comprises an isolated nucleic acid. In the case of probes, the nucleic acid further comprises a label (e.g., a radionuclide such as $^{32}P$ ATP or $^{35}S$) or a reporter molecule (e.g., a ligand such as biotin or an enzyme such as horseradish peroxidase). The [$^{32}P$]-ATP, [$^{35}S$]-dATP and [$^{35}S$]-methionine can be purchased, for example, from DuPont NEN (Wilmington, Del.). Probes can be used to identify the presence of a hybridizing nucleic acid sequence, e.g., an RNA in a sample or a cDNA or genomic clone in a library. Primers can be used, for example, for amplification of nucleic acid sequences, e.g., by the polymerase chain reaction (PCR). See, e.g., Innis et al. (eds.) 1990 *PCR Protocols: A Guide to Methods and Applications*, Academic Press: San Diego. The preparation and use of probes and primers is described, e.g., in Sambrook et al. (1989) or Ausubel et al. (1987). The genes of homologs of RNA of the invention in other species can be obtained by generating cDNA from RNA from such species using any technique known in the art, such as using Riboclone cDNA Synthesis Systems AMV RT (Promega, Madison, Wis.), then probing such cDNA with radiolabeled primers containing various portions (e.g. 30 or 40 bases long) of the sequences disclosed herein. To obtain homologs of the proteins of the invention, degenerate primers can encode the amino acid sequence of the disclosed *E. coli* protein but differ in codon usage from the sequences disclosed.

Antisense and ribozyme nucleic acids capable of specifically binding to sequences of the invention are also useful for interfering with gene expression.

The nucleic acids of the present invention (whether sense or anti-sense, and whether encoding the genes of the invention, or a homolog, variant, fragment or complement thereof) can be produced in large amounts by replication of a suitable recombinant vector comprising DNA sequences in a compatible host cell. Alternatively, these nucleic acids can be chemically synthesized, e.g., by any method known in the art, including, but not limited to, the phosphoramidite method described by Beaucage et al. 1981 *Tetra Letts* 22:1859–1862, and the triester method according to Matteucci et al. 1981 *J Am Chem Soc* 103:3191, preferably using commercial automated synthesizers. The purification of nucleic acids produced by the methods of the present invention can be achieved by any method known in the art including, but not limited to, those described, e.g., in Sambrook et al. (1989), or Ausubel et al. (1987). Numerous commercial kits are available for DNA purification including Qiagen plasmid mini DNA cartridges (Chatsworth, Calif.).

The nucleic acids of the present invention can be introduced into host cells by any method known in the art, which vary depending on the type of cellular host, including, but not limited to, electroporation; transfection employing calcium chloride, rubidium chloride calcium phosphate, DEAE-dextran, or other substances; microprojectile bombardment; P1 transduction; use of suicide vectors; lipofection; infection (where the vector is an infectious agent, such as a retroviral genome); and other methods. See generally, Sambrook et al. (1989), and Ausubel et al. (1987). The cells into which these nucleic acids have been introduced also include the progeny of such cells.

A polypeptide "fragment", "portion", or "segment" is a stretch of amino acid residues of at least about 7 to 19 amino acids (or the minimum size retaining an antigenic determinant). A fragment of the present invention can comprise a portion of at least 20 amino acids of the protein sequence, at least 30 amino acids of the protein sequence, at least 40 amino acids of the protein sequence, at least 50 amino acids of the protein sequence, or all or substantially all of the protein sequence. In addition, the invention encompasses polypeptides which comprise a portion of the sequence of the lengths described in this paragraph, which further comprise additional amino acid sequences on the ends or in the middle of sequences. The additional amino acid sequences can, for example, comprise another protein or a functional domain thereof, such as signal peptides, membrane-binding moieties, etc.

A polynucleotide fragment of the present invention can comprise a polymer of at least six bases or basepairs. A fragment of the present invention can comprise at least six bases or basepairs, at least 10 bases or basepairs, at least twenty bases or basepairs, at least forty bases or base pairs, at least fifty bases or basepairs, at least one hundred bases or basepairs, at least one hundred fifty bases or basepairs, at least two hundred bases or basepairs, at least two hundred fifty bases or basepairs, at least three hundred bases or basepairs of the gene sequence. In addition, the invention encompasses polynucleotides which comprise a portion of the sequence of the lengths described in this paragraph, which further comprise additional nucleic acid sequences on the 5' or 3' end or inserted into the sequence. These additional sequences can, for example, encode a coding region of a gene or a functional domain thereof or a promoter.

The terms "isolated", "pure", "substantially pure", and "substantially homogenous" are used interchangeably to describe a polypeptide, or polynucleotide which has been separated from components which naturally accompany it. A monomeric protein or a polynucleotide is substantially pure when at least about 60 to 75% of a sample exhibits a single polypeptide or polynucleotide sequence. A substantially pure protein or polynucleotide typically comprises about 60 to 90% by weight of a protein or polynucleotide sample, more usually about 95%, and preferably will be over about 99% pure.

Protein or polynucleotide purity or homogeneity may be indicated by a number of means, such as polyacrylamide gel electrophoresis of a sample, followed by visualizing a single band upon staining the gel. For certain purposes higher resolution can be provided by using high performance liquid chromatography (HPLC) or other means well known in the art for purification.

An RNA or a protein is "isolated" when it is substantially separated from the contaminants which accompany it in its natural state. Thus, a polypeptide which is chemically synthesized or expressed as a recombinant protein, i.e., an expression product of an isolated and manipulated genetic sequence, is considered isolated. A recombinant polypeptide is considered "isolated" even if expressed in a homologous cell type.

A polypeptide can be purified from cells in which it is produced by any of the purification methods known in the art. For example, such polypeptides can be purified by immunoaffinity chromatography employing, e.g., the antibodies provided by the present invention. Various methods of protein purification include, but are not limited to, those described in *Guide to Protein Purification*, ed. Deutscher, vol. 182 of *Methods in Enzymology* Academic Press, Inc., San Diego, 1990 and Scopes, 1982 *Protein Purification: Principles and Practice* Springer-Verlag, New York.

Polypeptide fragments of the protein of the invention are first obtained by digestion with enzymes such as trypsin, clostripain, or *Staphylococcus* protease, or with chemical agents such as cyanogen bromide, O-iodosobenzoate, hydroxylamine or 2-nitro-5-thiocyanobenzoate. Peptide fragments can be separated by reversed-phase HPLC and analyzed by gas-phase sequencing. Peptide fragments are used in order to determine the partial amino acid sequence of a polypeptide by methods known in the art including but not limited to, Edman degradation.

The present invention also provides polyclonal and/or monoclonal antibodies capable of specifically binding to a polypeptide of the invention, or homolog, fragment, complement or derivative thereof. Antibodies can also be produced which bind specifically to a polynucleotide of the invention, such as an RNA of the invention or homolog, fragment, complement or derivative thereof, and may be produced as described in, for example, Thiry 1994 *Chromosoma* 103: 268–76; Thiry 1993 *Eur J Cell Biol* 62:259–69; Reines 1991 *J Biol Chem* 266:10510–7; Putterman et al. 1996 *J Clin Invest* 97:2251–9; and Fournie 1996 *Clin Exp Immunol* 104:236–40. Antibodies capable of binding to polypeptides or polynucleotides of the invention can be useful in detecting protein, in titrating protein, for quantifying protein, for purifying protein or polynucleotide, or for other uses.

For production of polyclonal antibodies, an appropriate host animal is selected, typically a mouse or rabbit. The substantially purified antigen, whether the whole polypeptide, a fragment, derivative, or homolog thereof, or a polypeptide coupled or fused to another polypeptide, or polynucleotide or homolog, derivative, complement or fragment thereof, is presented to the immune system of the host by methods appropriate for the host, commonly by injection into the footpads, intramuscularly, intraperitoneally, or intradermally. Peptide fragments suitable for raising antibodies can be prepared by chemical synthesis, and are commonly coupled to a carrier molecule (e.g., keyhole limpet hemocyanin) and injected into a host over a period of time suitable for the production of antibodies. The sera are tested for immunoreactivity to the protein or fragment. Monoclonal antibodies can be made by injecting the host with the protein polypeptides, fusion proteins or fragments thereof and following methods known in the art for production of such antibodies (Harlow et al. 1988 *Antibodies: A Laboratory Manual*, Cold Spring Harbor Laboratories).

An immunological response is usually assayed with an immunoassay, a variety of which are provided, e.g., in Harlow et al. 1988, or Goding 1986 *Monoclonal Antibodies: Principles and Practice*, 2d ed., Academic Press, New York), although any method known in the art can be used.

Monoclonal antibodies with affinities of $10^8$ M$^{-1}$, preferably $10^9$ to $10^{10}$, or stronger are made by standard procedures as described, e.g., in Harlow et al. 1988, or Goding 1986. Briefly, appropriate animals are immunized with the antigen by a standard protocol. After the appropriate period of time, the spleens of such animals are excised and individual spleen cells fused to immortalized myeloma cells. Thereafter the cells are clonally separated and the supernatants of each clone are tested for their production of an appropriate antibody specific for the desired region of the antigen.

Other suitable techniques of antibody production include, but are not limited to, in vitro exposure of lymphocytes to the antigenic polypeptides or selection of libraries of antibodies in phage or similar vectors (Huse et al. 1989 *Science* 246:1275–1281).

Frequently, the polypeptides and antibodies are labeled, either covalently or noncovalently, with a substance which provides for a detectable signal. A wide variety of labels and conjugation techniques are known. Suitable labels include, but are not limited to, radionuclides, enzymes, substrates, cofactors, inhibitors, fluorescent agents, chemiluminescent agents, magnetic particles. Also, recombinant immunoglobulins can be produced by any method known in the art.

Identification of Novel Small RNAs Using Comparative Genomics and Microarrays

As a starting point for detecting novel sRNAs in *E. coli*, we considered a number of common properties of the previously identified sRNAs that might serve as a guide to identify genes encoding new sRNAs. We are defining sRNA as relatively short RNAs that do not function by encoding a complete ORF. Of the 13 small RNAs known when this work begun, we were struck by the high conservation of these genes between closely related organisms. In most cases, the conservation between *E. coli* and *Salmonella* was above 85%, whereas that of the typical gene encoding an ORF was frequently below 70%. Conservation tests on random noncoding regions of the genome suggested that extended conservation in intergenic regions was unusual enough to be used as an initial parameter to screen for new sRNA genes. We therefore tested this approach to look for novel sRNAs in the *E. coli* genome.

All known sRNAs are encoded within intergenic (Ig) regions (defined as regions between ORFs). A file containing all Ig sequences from the *E. coli* genome (Blattner, F. R. et al. 1997 *Science* 277:1453–1474) was used as a starting point for our homology search. We arbitrarily chose the 1.0- to 2.5-Mb region of the 4.6-Mb *E. coli* genome to test and refine our approach and developed the following steps for searching the full *E. coli* genome.

Figure 1B:
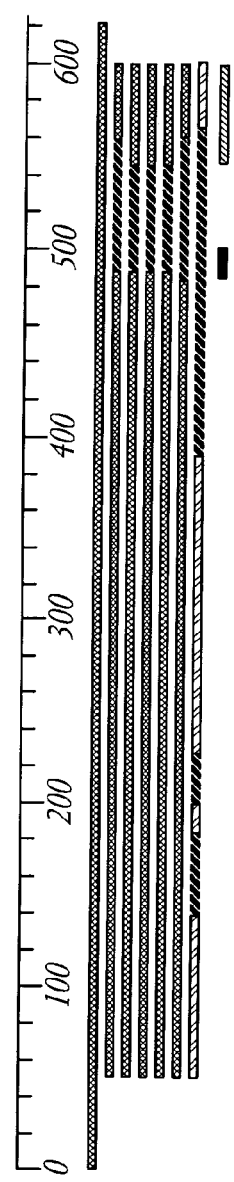
Figure 1C:
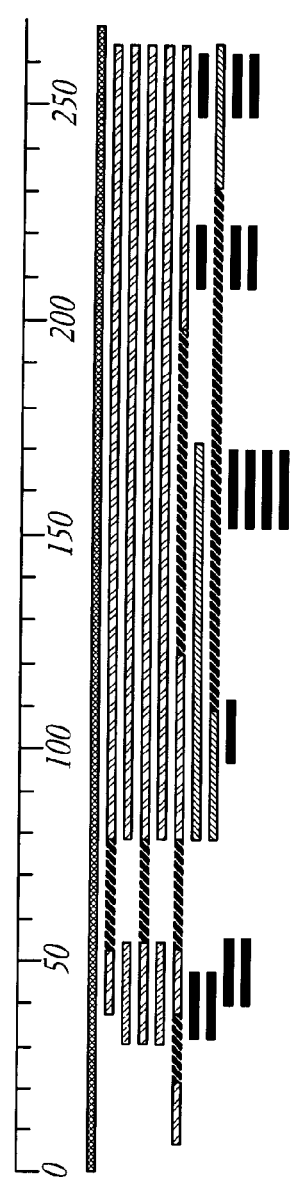

All Ig regions of 180 nucleotides (nt) or larger were compared to the NCBI Unfinished Microbial Genomes database using the BLAST program (Altschul, S. F. et al. 1990 *J Mol Biol* 215:403–410). These 1097 Ig regions were rated based on the degree of conservation and length of the conserved region when compared to the closely related *Salmonella* and *Klebsiella pneumoniae* species. The highest rating was given to Ig regions with a high degree of conservation (raw BLAST score of >80) over at least 80 nt (see below for explanation of ratings). Note that most promoters do not meet these length and conservation requirements. FIG. 1 shows a set of BLAST searches for three known sRNAs (RprA RNA, CsrB RNA, OxyS RNA), three Ig regions with high conservation (#14, #17, #52) and one Ig region with intermediate conservation (#36). Some Ig regions had a large number of matches, often to several chromosomal regions of the same organism. These Ig regions were noted and many were found to contain tRNAs, rRNAs, REP, or other repeated sequences. The 40 highly conserved Ig regions containing tRNAs and/or rRNAs were eliminated from our search, as these regions were complicated in their patterns of conservation.

Next the orientation and identity of the ORFs bordering the Ig regions were determined using the Colibri database, an annotated listing of all *E. coli* genes and their coordinates. Inconsistencies between the Colibri database and our original file led to the reclassification of some Ig regions as shorter than 180 nt, and these were not analyzed further. Of the remaining 1006 Ig regions, 13 contained known small RNAs, 295 were in the highest conservation group, 88 showed intermediate conservation, and 610 showed no conservation.

The location of the conservation relative to the orientation of the flanking ORFs was an important consideration in choosing candidates for further analysis. In many cases (132/295 Ig regions), the conserved region was just upstream of the start of an ORF, consistent with conservation of regulatory regions, including untranslated leaders. Cases where the conserved region was >50 nt from an ORF start or extended over more than 150 nt in length (RprA RNA, CsrB RNA, OxyS RNA, #17, and #52 in FIG. 1), or where the bordering ORFs ended rather than started at the Ig region (#14 in FIG. 1), were considered better candidates for novel sRNAs.

Published information on promoters and other known regulatory sites within conserved regions of promising candidates was tabulated and used to eliminate many candidates in which the conservation could be attributed to previously identified promoter or 5' untranslated leaders. Finally, the remaining candidate regions were examined for sequence elements such as potential promoters, terminators, and inverted repeat regions. We considered evidence for possible stem-loops, in particular those with characteristics of rho-independent terminators, as especially indicative of possible sRNA genes (Table 1).

Using these criteria, together with microarray expression data (see below), a set of 59 candidates was selected (Table 1). Candidates 1–18 were chosen in the first round of screening of the 1.0- to 2.5-Mb region; some of these candidates would not have met the higher criteria applied to the rest of the genome.

TABLE 1 sRNA Candidates

| No.[a] | Ig Start | Ig Length | Flanking Genes | Strand[b] | Selection Criteria[c] | Microarray Detection[d] | Northern Detection[e] | Interpretation of Conservation[f] |
|---|---|---|---|---|---|---|---|---|
| 1 | 1019277 | 359 | ompA/sulA | < < | C (4), S | < | large | known ompA leader |
| 2 | 1102420 | 754 | csgD/csgB | < > | C (4), L | none | faint large | known csgD leader, promoter |
| 3 | 1150625 | 213 | fabG/acpP | > > | C* (4), S | > | multiple, 300+ nt | known acpP mRNA & operon leader |
| 4 | 1194145 | 201 | ymfC/icd | < > | C* (0), S | > | large | leader |
| 5 | 1297345 | 476 | adhE/ychE | < > | C (4), L | none | large | known adhE leader |
| 6 | 1298466 | 740 | yhcE/oppA | > > | C (2), L, S | > | large + faint others | leader, promoter? |
| 7 | 1328693 | 376 | yciN/topA | < > | C (4) | none | large | known leader, promoter |
| 8 | 1407055 | 480 | ydaN/dbpA | > > | C (4), L | none | none | predict sRNA |
| 9 | 1515024 | 314 | ydcW/ydcX | > > | C (4), L, S | <, > | 180 nt (<) | mRNA, 31 aa ORF |
| 10 | 1671526 | 411 | ydgF/ydgG | < > | C (4), L, T | none | none | promoter/leader? |
| 11 | 1755132 | 313 | pykF/lpp | > > | C (4) | > (rif) | 300 nt | known lpp mRNA |
| 12 | 1762411 | 550 | ydiC/ydiH | < < | C (4), T | none | 60 nt (<) | sRNA |
| 13 | 1860454 | 341 | yeaA/gapA | < > | C (4), S | > (rif) | large | known gapA leader, promoter? |
| 14 | 2165049 | 278 | yegQ/orgK | > < | C (4), L, S | > | 86 nt (>) | sRNA |
| 15 | 2276258 | 335 | yejG/bcr | < < | C (4), L, S | < | large | leader |
| 16 | 2403093 | 633 | nuoA/lrhA | < < | C (4), L, S | < | large + 300 nt | known processed leader |
| 17 | 2588726 | 540 | acrD/yffB | > > | C (4), S, I | < | 175, 266 nt (<) | mRNA, 19 aa ORF |
| 18 | 1339749 | 196 | yciM/pyrF | > > | C (3), S* | none | none | promoter/leader? |
| 19 | 450835 | 462 | cyoA/ampG | < < | C (4), S* | > | faint large | promoter/leader? |
| 20 | 753692 | 708 | gltA/sdhC | < > | C* (4), S | < (rif) | faint large | known gltA, sdhC leaders |
| 21 | 986206 | 605 | ompF/asnS | < < | (4), S*, I, P, T | < (rif), > | large | known ompF leader, promoter |
| 22 | 2651357 | 823 | sseA/sseB | > < | C (4), L, S, I, T | > (rif) | 320 nt (>) | sRNA |
| 24 | 3348110 | 223 | elbB/arcB | < < | C* (4), S* | <, > | 45 nt (>) | sRNA |
| 25 | 3578437 | 332 | yhhX/yhhY | < > | C (4), L, P, T | none | 90 nt (<) | sRNA |
| 26 | 3983621 | 681 | aslA/hemY | < < | C (4), T | > | 210 nt (>) | sRNA |
| 27 | 4275510 | 548 | soxR/yjcD | > > | C (4), L, S*, T | < | 140 nt (<) | sRNA |
| 28 | 4609568 | 412 | osmY/yjjU | > > | C (4), L, S* | <, > (rif) | 350 nt (>) | mRNA, 53 aa ORF |
| 29 | 454011 | 346 | bolA/tig | > > | C* (4), S, I | > (rif). | large | leader or operon |
| 30 | 668152 | 370 | ybeB/cobC | < < | C (4), L, S*, I, P | <, >(rif) | large (>) | leader/promoter? |
| 31 | 887180 | 180 | ybjK/ybjL | > < | C (4), L | none | 80 nt (<) | sRNA |
| 32 | 2590752 | 343 | dapE/ypfH | > < | C (0), L, S | <, > | none | 66 aa ORF |
| 33 | 2967000 | 684 | ygdP/mutH | < > | C* (4) | none | none | promoter/leader? |
| 34 | 3672003 | 413 | yhjD/yhjE | > > | C* (4) | none | none | promoter/leader? |
| 35 | 3719676 | 284 | yiaZ/glyS | < < | C (4), L, P | none | large | leader/promoter? |
| 36 | 3773784 | 508 | mtlR/yibL | > > | (2), S* | < (rif) | 500 nt (<) | mRNA, 69 aa ORF |
| 37 | 4638109 | 402 | yjjY/lasT | > > | C (4), L, P, F | > | none/faint | known arcA leader |
| 38 | 4048313 | 614 | yihA/yihI | < > | C* (4), S, T | > (rif) | 270 nt (>) | sRNA |
| 39 | 279100 | 512 | afaB/yagB | < < | C (4), L, S* | <, > | faint large | IS30, leader/promoter? |

TABLE 1-continued sRNA Candidates

| No.[a] | Ig Start | Ig Length | Flanking Genes | Strand[b] | Selection Criteria[c] | Microarray Detection[d] | Northern Detection[e] | Interpretation of Conservation[f] |
|---|---|---|---|---|---|---|---|---|
| 40 | 852161 | 245 | b0816/ybiQ | < > | C (4), L, P | none | 205 nt (<) | sRNA |
| 41 | 2974037 | 584 | aas/galR | < > | C (4), L, S, T | <, > | 89, 83 nt (<) | sRNA |
| 42 | 2781229 | 432 | pinH/ypjB | < < | C (1), L, T | none | none | not conserved |
| 43 | 3192539 | 424 | yqiK/rfaE | > < | C* (4), L, S | <, > | none | predicted sRNA |
| 44 | 3245066 | 347 | exuR/yqjA | > > | C (4), L | > | none | promoter/leader? |
| 45 | 3376287 | 221 | rplM/yhcM | < < | C* (4), (S), T | < (rif) | large | leader |
| 46 | 2531398 | 386 | cysK/ptsH | > > | C (4), S*, T | <, > (rif) | large | known ptsH leader |
| 47 | 4403561 | 207 | purA/yjeB | > > | C (4), S*, I | > | large | leader/promoter? |
| 48 | 1239170 | 391 | dadX/ycgO | > < | C (4), L | none | none | IS end |
| 49 | 1306670 | 373 | cls/kch | < < | C* (4) | none | 250 nt (>) | mRNA, 57 aa ORF |
| 50 | 1620541 | 446 | ydeE/ydeH | > < | C (4), L, I | > | 185, 220 nt (>) | mRNA, 31 aa ORF |
| 51 | 1903281 | 377 | yobD/yebN | > > | C (4), L | none | none | promoter/leader? |
| 52 | 1920997 | 395 | pphA/yebY | < < | C (4), L, S* | <, > | 275 nt (>), 100 nt (<) | sRNA |
| 53 | 1932629 | 237 | edd/zwf | < < | C (4) | < | none | promoter/leader? |
| 54 | 2085091 | 263 | yeeF/yeeY | < < | C (4), T | < | large | leader |
| 55 | 2151151 | 740 | yegL/yegM | < > | C (4), L | > | 143 nt + others (>) | sRNA |
| 56 | 2494583 | 497 | ddg/yfdZ | > < | C (4), L | < | none | known ORF |
| 57 | 3717395 | 283 | yiaG/cspA | > > | C* (4), S* | <, > | large | known cspA leader |
| 58 | 4177159 | 415 | rplA/rplJ | > > | C (4), S* | <, > | large | known operon |
| 59 | 1668974 | 396 | ynfM/asr | > > | (2), S* | < | none | promoter/leader? |
| 60 | 2033263 | 591 | yedS/yedU | > > | (1), S* | <, > | none | not conserved |
| 61 | 3054807 | 394 | ygfA/serA | > < | (1), D | <, > | 139 nt (>) | sRNA |

[a]Candidate numbers. #23 was not analyzed; the region of conservation corresponds to a published leader sequence. Candidate #61 was added because it is homologous to candidate #43 and the duplicated regions within #55 (see Text and Table 2).
[b]Orientation of flanking genes. > and < denote genes present on the clockwise (Watson) or counterclockwise (Crick) strand of the E. coli chromosome, respectively.
[c]Criteria used for selection of candidates: C, conservation; C*, long conservation; (#), conservation score. Ig regions were assigned scores on the basis of BLAST searches (see text below). #4 and #32 were rerated from 4 (conserved) to 0 on reanalysis of the endpoints of the flanking ORF (#4) and information on an ORF within the g region (#32). L, location of conservation either far from 5' end of flanking gene or near 3' end of gene; S, signal detected in microarray experiments; S*, microarray signal on opposite strand to flanking genes; I, inverted repeat; P, predicted promoter; T, predicted terminator; D, duplicated gene.
[d]Detection on high-density oligonucleotide probe arrays. > <, orientation of signal as in b. Rif, signals present after 20 min treatment with rifampicin.
[e]Northern analysis of RNA extracted from MG1655 cells grown in three conditions (LB medium, exponential phase; minimal medium, exponential phase; LB medium, stationary phase). Strand specific probes were used for sRNA and mRNAs encoding novel ORFs (orientation noted < or > as in b); double stranded DNA probes were used for the rest. For #43, bands were originally detected with a double stranded probe, but appear to be from homologs (see text). Large, >400 nt.
[f]Interpretation of high conservation was based on microarray and Northern analyses as well as literature. mRNAs, small RNA transcripts predicted to encode new polypeptides (see text). "known leaders", literature references supported the existence of leaders corresponding to conservation. For #37, conservation is consistent with the leader of the arcA gene (Compan, I. and Touati, D. 1994 Mol Microbiol 11: 955–964). The ORF noted for #56 is described in Seoane, A. S. and Levy, S. B. 1995 J Bacteriol 177: 530–535; and Bouvier, J. et al. 1992 J Bacteriol 174: 5265–5271; see GenBank entry BAA16347.1. The IS sequence fragment in the conserved region of #48 is homologous to that described by McVeigh, A. et al. 2000 Infect Immun 68: 5710–5715. "leaders", a large band on Northern analysis, coupled with conservation near the 5' end of an ORF. "promoter/leader?", absence of RNA signal, coupled with conservation near the 5' end of a gene. "leader/promoter?", RNA signal from microarray or Northern analyses suggested a leader, while the conservation is far from the expected position of a leader. "leader or operon", (for #29) microarray analysis suggested a continuous transcript throughout Ig. "predicted sRNAs", (for #8 and #43) Igs contain the hallmarks expected for an sRNA, but RNA transcripts were not detected. Igs encoding sRNAs also may include leaders; this is not included in the conclusion column.

Selecting Candidate Genes by Whole Genome Expression Analysis

In an independent series of experiments, high-density oligonucleotide probe arrays were used to detect transcripts that might correspond to sRNAs from Ig regions. Total RNA isolated from MG1655 cells grown to late exponential phase in LB medium was labeled for probes or used to generate cDNA probes (see text below). From a single RNA isolation each labeling approach was carried out in duplicate and individually hybridized to high-density oligonucleotide microarrays. The high-density oligonucleotide probe arrays used are appropriate for this analysis as they have probes specific for both the clockwise (Watson) and counterclockwise (Crick) strands of each Ig region as well as for the sense strand of each ORF. The resulting data from the four experiments were analyzed to examine global expression within Ig regions, as well as neighboring ORFs.

Figure 2A:
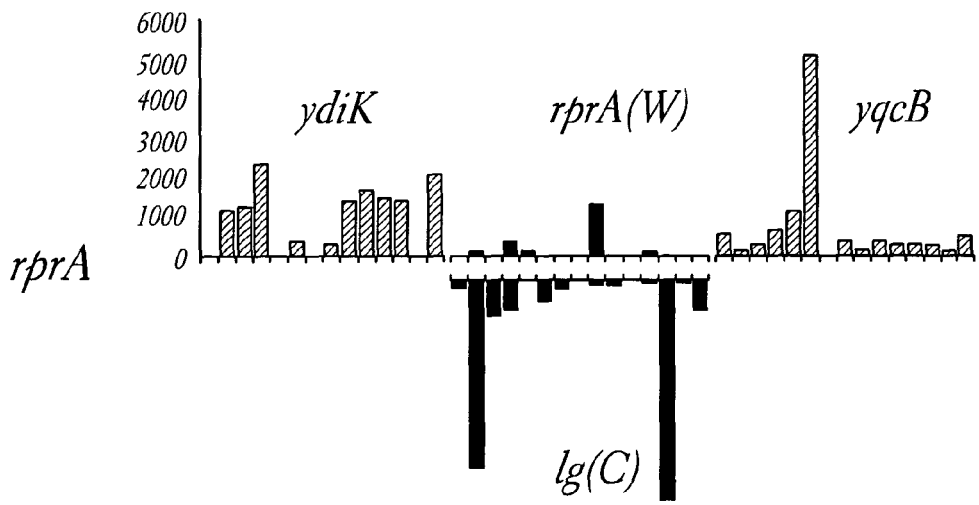
FIG. 2 is the expression profile across high-density oligonucleotide arrays for representative Ig regions. Probe intensities are shown for the indicated Ig regions (solid bars) and the flanking ORFs (hatched bars), calculated from the perfect match minus the mismatch intensities. All negative differences were set to zero. The data shown are for one experiment using cDNA probes, but similar results were seen in the duplicate experiment and with directly labeled RNA probes. The Ig regions and each flanking gene generally contain 15 interrogating probes. Upward bars correspond to genes transcribed on the Watson (W, clockwise) strand and downward bars correspond to genes transcribed on the Crick (C, counterclockwise) strand. The C strand signal for the CsrB Ig region corresponds well with the known location of the csrB gene. Similarly for the RprA Ig region, the W strand signal corresponds with the location of the rprA gene, but only one probe is positive. The W strand signal for #14 and the C strand signal for #17 overlap well with the conserved regions shown in the BLAST analysis in FIG. 1. #36 was chosen for further analysis because of the strong C strand signal; both flanking ORFs are on the W strand. For #52, low levels of expression were seen on both strands; the very low level for probes in the middle of the Ig on the C strand overlapped best with the conserved region found by the BLAST searches (FIG. 1).
Figure 2B:
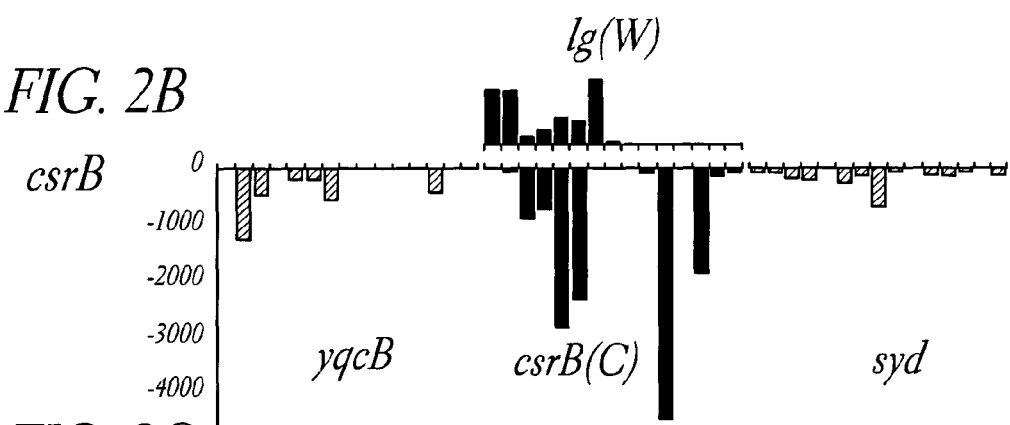
Figure 2C:
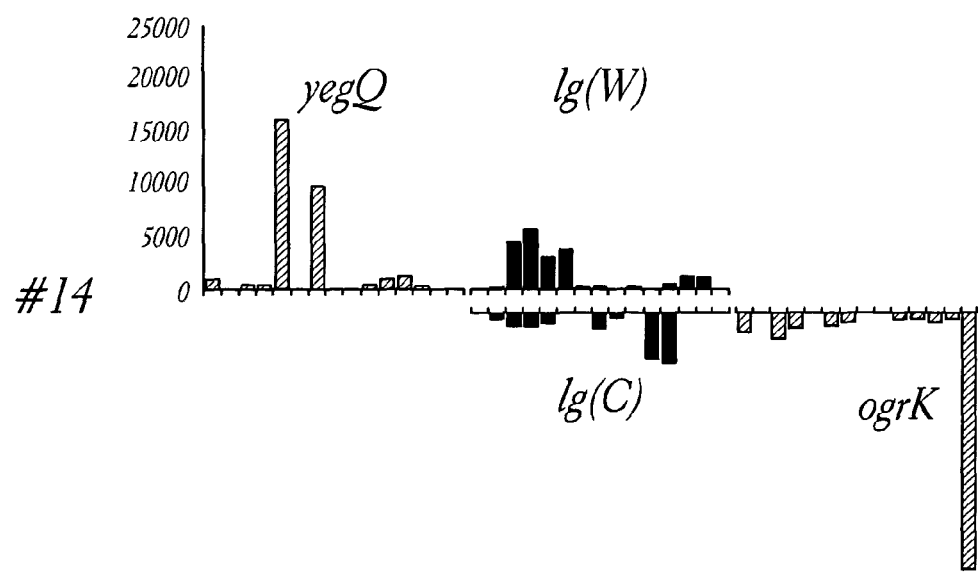

Our criteria for analyzing the microarray data evolved during the course of this analysis. Stringent criteria (longer transcripts in the Ig region, higher expression levels) identified many of the previously known sRNAs but did not uncover many strong candidates for new small RNAs. More relaxed criteria (shorter transcripts, lower expression levels) gave a very large number of candidates and therefore were not by themselves useful as the initial basis for identifying candidates. However, this data was very useful as an additional criterion for selection of candidate regions based on the conservation approach. Detection of a transcript by microarray on the strand opposite to that of surrounding ORFs was considered a strong indicator of an sRNA (S* in Table 1). Microarray data contributed to the selection of 34 of 59 candidates (Table 1). Examples of the different types of expression observed in microarray experiments are shown in FIG. 2. Signal corresponding to CsrB RNA clearly is detected on the Crick (C) strand. #17 and #36 have a transcript in the Ig region on the opposing strand (C) to that for the flanking genes (Watson; W). However, the expression patterns were not as obvious in many cases, either because expression levels were low or because the pattern of expression could be interpreted in a number of ways. For instance, very little expression was detected for RprA RNA encoded on the W strand, and there is unexplained signal detected from the opposite strand of the rprA and csrB Ig regions. #14 and #52 also had some expression on each strand (FIG. 2). #14 proved to express a small RNA from the Watson strand, while #52 expresses sRNAs from each strand (see below and Table 2).

tor rifampicin was added to cells for 20 min prior to harvesting the RNA with the intention of enriching for stable RNAs. Many of the known sRNAs can be detected after the rifampicin treatment. Of the 59 candidates in Table 1 twelve retained a hybridization signal (marked rif in Table 1), and four of these proved to correspond to small transcripts (see below). Other rif resistant transcripts detected in Ig regions appeared to be due to highly expressed leaders.

TABLE 2

Novel sRNAs and Predicted Small ORFs[a]

| No. | Gene | Minute | RNA Size[b,c,d] | Strand[e] | Expression[f] | Hfq Binding[g] | Effect on rpoS-lacZ[h] S | M | Other Information[j] |
|---|---|---|---|---|---|---|---|---|---|
| 12 | rydB | 38 | 60[b] | < < < | M >> S > E | NT | 0.4 | 1.0 | |
| 14 | ryeE | 47 | 86[b] | > > < | E, S > M | + (E) | 0.25 | 1.2 | bordered by cryptic prophage |
| 22 | ryfA | 57 | 320[c] | > > < | E, M | NT | NT | NT | PAIR3 (Rudd, K. E. 1999 Res Microbiol 150: 653–664) |
| 24 | ryhA | 72 | 45[b] | < > < | S >> M > E | + (S) | 1.0 | 1.9 | 105, 120 nt, present S >> M > E 105 nt binds Hfq (+, S) |
| 25 | ryhB | 77 | 90[b] | < < > | M >> S | + (M) | 1.2 | 0.4 | multicopy plasmid restricts growth on succinate |
| 26 | ryiA | 86 | 210[b] | < > < | E > M, S | + (E) | 0.9 | 1.5 | 155 nt, present M > E, S |
| 27 | ryjA | 92 | 140[b] | > < > | S >> M | − (S) | NT | NT | |
| 31 | rybB | 19 | 80[b] | > < < | S >> M | + (S) | 1.0 | 2.3 | |
| 38 | ryiB | 87 | 270[b] | < > > | M > S >> E | − (M) | 1.0 | 1.6 | CsrC (Romeo, pers. commun.) |
| 40 | rybA | 18 | 205[b] | > < > | S > M > E | − (S) | 1.2 | 1.5 | ladder up from 255, 300 nt, present S > M > E |
| 41-I | rygA | 64 | 89[b] | < < > | S >> M, E | + (S) | 1.3[i] | 1.7[i] | PAIR2 (Rudd, K. E. 1999 Res Microbiol 150: 653–664) |
| 41-II | rygB | 64 | 83[b] | < > > | S, E > M | + (S) | 1.3[i] | 1.7[i] | PAIR2 (Rudd, K. E. 1999 Res Microbiol 150: 653–664) |
| 52-I | ryeA | 41 | 275[b] | < > < | M > E > S | −/+ (M) | 1.1[i] | 1.0[i] | 148, 152, 180 nt (+ others), present M, S |
| 52-II | ryeB | 41 | 100[b] | < < < | S >> M | + (S) | 1.1[i] | 1.0[i] | 70 nt, present S >> M |
| 55-I | ryeC | 46 | 143[c] 107[c] | < > > | S > M > E M > E, S | NT | 1.2 | 1.6 | QUAD1a (Rudd, K. E. 1999 Res Microbiol 150: 653–664) |
| 55-II | ryeD | 46 | 137[c] 102[c] | < > > | M > E > S M > E | NT | NT | NT | QUAD1b (Rudd, K. E. 1999 Res Microbiol 150: 653–664) |
| 61 | rygC | 65 | 139[c] 107[c] | > > < | S >> M > E S, M > E | NT | NT | NT | QUAD1c (Rudd, K. E. 1999 Res Microbiol 150: 653–664) |
| 8 | rydA | 30 | 139[d] | >(>)> | none | NT | NT | NT | Expression not detected; predicted sRNA |
| 43 | rygD | 69 | 143[d] | >(<)< | none | NT | NT | NT | QUAD1d (Rudd, K. E. 1999 Res Microbiol 150: 653–664) Expression not detected |
| 9 | yncL | 32 | 180[b] | > < > | S > M > E | +/− (S) | NT | NT | 31 aa ORF |
| 17 | ypfM | 55 | 266[b] | > < > | E >> M | −/+ (E) | 2.0 | 1.5 | 19 aa ORF 175 nt, present E, M |
| 28 | ytjA | 99 | 305[b] | > > > | S > M | NT | NT | NT | 53 aa ORF |
| 36 | yibT | 81 | 500[b] | > < > | S >> E, M | NT | 1.3 | 1.0 | 69 aa ORF |
| 49 | yciY | 28 | 250[b] | < > < | E, M | NT | NT | NT | 57 aa ORF |
| 50 | yneM | 35 | 185[b] 220[b] | > > < | S M > E | NT | NT | NT | 31 aa ORF |

[a]Table is divided into three sections: detected sRNAs, predicted sRNAs and detected RNAs predicted to encode small ORFs.
[b,c,d]RNA sizes estimated from Northern analyses using [b]single stranded RNA probes or [c]oligonucleotide probes, or [d]from predictions resulting from sequence analysis (see text).
[e]> <denotes orientation of sRNA and flanking genes as in Table 1.
[f]Relative expression in three growth conditions: E, LB medium, exponential phase; M, minimal medium, exponential phase; and S, LB medium, stationary phase.
[g]RNA coimmunoprecipitation with Hfq as detected by Northern analysis: +, strong binding (>30% of RNA bound); +/−, weak binding (5–10%); −/+, minimal binding (<5%), and −, no detectable binding. E, M, S refer to cell growth conditions as in f. NT, not tested.
[h]Expression of rpoS-lacZ fusion in the presence of multicopy plasmids carrying intergenic regions. Activity was measured in stationary phase in LB medium (S) or minimal medium (M) and normalized to the activity of the vector control in the same experiment. In parallel experiments, cells carrying the vector alone gave 1.3–2 (S) and 0.7–2.6 (M) units, cells carrying pRS-DsrA plasmid gave a 4.9 fold increase (S) and 12 fold increase (M); cells carrying pRS-RprA plasmid gave 3.1 fold (S) and 3.3 fold (M) increase. Results in table are average of at least three independent assays. Values in bold were considered significantly different from the control. NT, not tested.
[i]#41 and #52 each express two sRNAs so it is not possible to assign a phenotype to a given small RNA. Thus far there is no evidence for a strong phenotype for either candidate.
[j]Included is information about additional RNA bands detected in Northern analysis.

Given that a number of the known sRNAs are relatively stable, we tested whether selection for stable RNAs might allow the microarray data to be more useful for de novo identification of sRNA candidates. The transcription inhibi- Small RNA Transcripts Detected by Northern Hybridization The final test for the presence of an sRNA gene was the direct detection of a small RNA transcript. The candidates in Table 1 were analyzed by Northern hybridization using RNA extracted from MG1655 cells harvested from three growth conditions (exponential phase in LB medium, exponential phase in M63-glucose medium, or stationary phase in LB medium). The microarray analysis discussed above used RNA isolated from cells grown to late exponential phase in LB medium, which is intermediate between the two LB growth conditions used for the Northern analysis. Initially, Northern analysis was carried out using double-stranded DNA probes containing the full Ig region for most candidates. In three cases (#8, #22, and #55) PCR amplification of the Ig region to generate a probe was not successful and therefore oligonucleotide probes were used for Northern analysis. Seventeen candidates gave distinct bands consistent with small RNAs, and one additional candidate gave a somewhat larger RNA, but the location of conservation was not consistent with a leader sequence for a flanking ORF (#36). In some of these cases, two or more RNA species were detected with a single Ig probe (Table 2, see also FIG. 3). One candidate (#43) gave a signal with the double stranded DNA probe, but contains regions duplicated elsewhere in *E. coli* that probably account for this signal (see below). Of the remaining 41 candidates, 17 gave no detectable transcript. These Ig regions could encode sRNAs expressed only under very specific growth conditions. For instance, #8 has all the sequence hallmarks of an sRNA gene (a well-conserved region preceded by a possible promoter and ending with a terminator), but has not been detected. Alternatively, the observed conservation could be due to nontranscribed regulatory regions. Fairly large RNAs were detected for another 24 candidates. Given the size of these transcripts together with data on the orientation of flanking genes and the location of conserved regions, it is likely these are leader sequences within mRNAs (Table 1).

Figure 3:
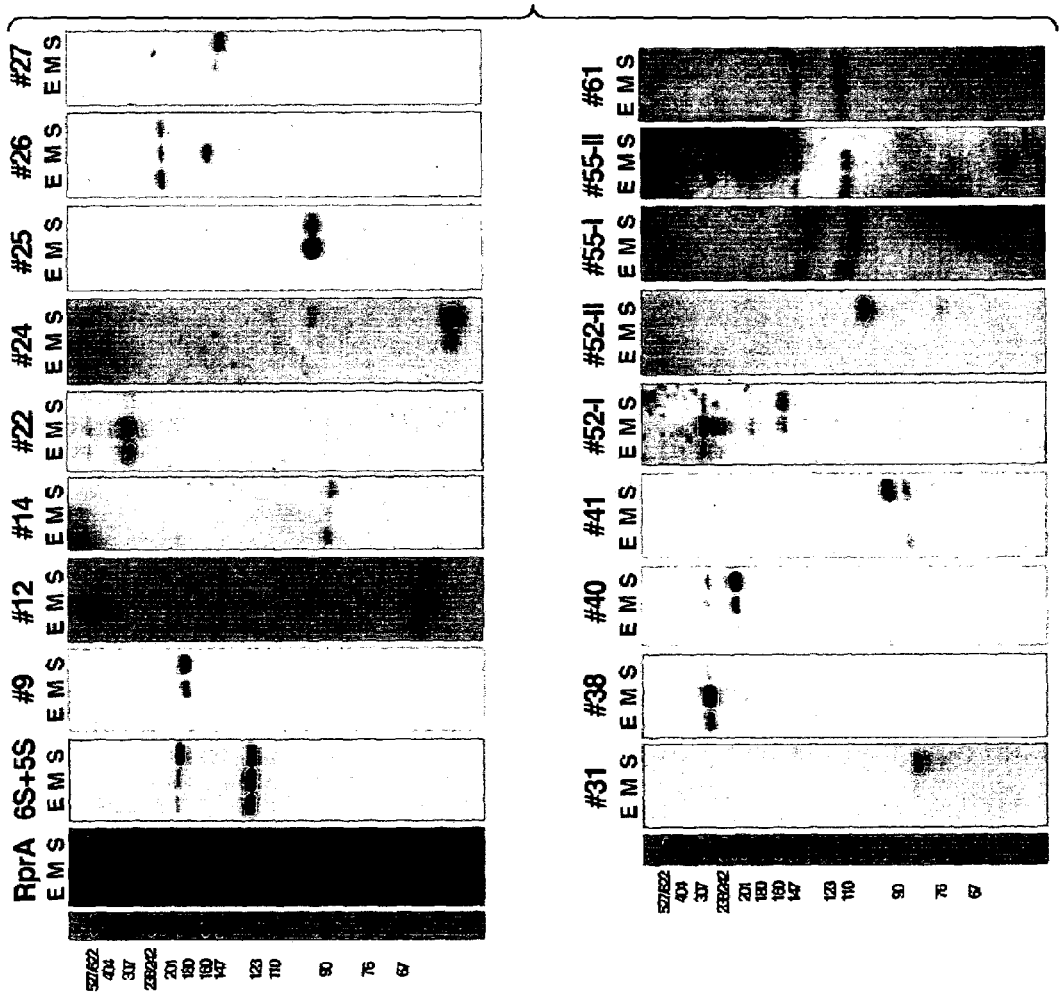
FIG. 3 shows detection of novel sRNAs by Northern hybridization. Northern hybridization using strand specific probes for each candidate was done on RNA extracted from MG1655 cells grown under three different growth conditions: (E), exponential growth in LB medium; (M), exponential growth in M63-glucose medium, and (S) stationary phase in LB medium. Five μg of total RNA was loaded in each lane. Exposure times were optimized for each panel for visualization here, therefore the signal intensity shown does not indicate relative abundance between sRNAs. Oligonucleotide probes were used for #12, #22, #55-I, #55-I, and #61; RNA probes were used for all other panels. DNA molecular weight markers (5'-end-labeled MspI digested pBR322 DNA) were run with each set of samples for direct estimation of RNA transcript length. One lane of DNA molecular weight markers are shown for comparison, but these are approximate sizes as there was slight variation in running of gels.

For candidates expressing RNAs not expected to be 5' untranslated leaders, Northern analysis was carried out with strand-specific probes to determine gene orientation (FIG. 3). For many of the candidates, we used sequence elements (see below) as well as expression information from the microarray experiments to predict which strand was most likely expressed; both strands were tested when predictions were unclear. The results from the strand-specific probes generally agreed with predictions and were used to estimate the RNA size (Table 2). Interestingly, in one case there is an sRNA expressed from both the W and C strand within the Ig (#52; FIG. 3). For #12, although no sRNA had been detected using a double stranded DNA probe, the presence of a potential terminator and promoter remained suggestive of the presence of an sRNA gene. Therefore, oligonucleotide probes also were used in Northern analysis of this candidate, and a small RNA transcript was detected (FIG. 3; Table 1).

Examination of expression profiles of the RNAs under different growth conditions gave an indication of specificity of expression. Some candidates were detected under all three growth conditions; others were preferentially expressed under one growth condition (FIG. 3; Table 2). For instance, #25 was present primarily during growth in minimal medium, consistent with the absence of detection in the whole genome expression experiment, which analyzed RNA isolated from cells grown in rich medium.

Sequence Predictions of sRNA Genes and ORFs

For the candidates expressing small RNA transcripts, the conserved sequence blocks (contigs) from *K pneumoniae*, the highest conserved *Salmonella* species, and in a few cases *Yersinia pestis*, were selected from the NCBI Unfinished Microbial Genome database and aligned with the *E. coli* Ig region using GCG Gap (Devereux, J. et al. 1984 *Nucleic Acids Res* 12:387–395). Multiple alignments were assembled by hand, and the conserved regions were examined for likely promoters and terminators and other conserved structures. Information from the alignments, together with results from strand-specific Northern and microarray expression analyses, allowed assignments of gene orientation, putative regulatory regions, and RNA length from the predicted starting and ending positions. Where a terminator sequence was very apparent (13 of 19 candidates), transcription was assumed to end at the terminator, and the observed size of the transcript was used to help identify possible promoters. The identification of promoters and terminators was less definite when there was only one species with conservation to *E. coli*.

As the alignments were assembled, the pattern of conservation in some cases was reminiscent of patterns expected from ORFs, with higher sequence variation in positions consistent with the third nucleotide of codons. GCG Map (Devereux, J. et al. 1984 *Nucleic Acids Res* 12:387–395) was used to predict translation in all frames for all of the candidate small RNAs. In six cases, the conservation and translation potential suggested the presence of a short ORF. In these cases, a ribosome-binding site and the potential ORF were well conserved, with the most variation in the third position of codons, but other elements of the predicted RNA were less well conserved. For example, #17 expresses an RNA of about 266 nt, containing a predicted ORF of only 19 amino acids. Within the predicted Shine-Delgarno sequence and ORF, only 9/80 positions showed variation for either *Klebsiella* or *Salmonella*, while the overall RNA is less than 60% conserved. We predict that for #17, as well as five others (Table 2), the detected RNA transcript is functioning as an mRNA, encoding a short, conserved ORF. An evaluation of both the new predicted ORFs and the untranslated sRNAs with GLIMMER, a program designed to predict ORFs within genomes, gave complete agreement with our designations (Delcher, A. L. et al. 1999 *Nucleic Acids Res* 27:4636–4641).

We have assigned gene names to all candidates that we have confirmed are expressed as RNAs (see Table 2). The genes we predict to encode ORFs were given names according to accepted practice for ORFs (Rudd, K. E. 1998 *Microbiol Mol Biol Rev* 62:985–1019). The genes that express sRNAs without evidence of conserved ORFs were named with a similar nomenclature: ryx, with ry denoting RNA and x indicating the 10 min interval on the *E. coli* genetic map.

We noted one instance of overlap in sequence between our new sRNAs. The conserved region within #43 is highly homologous to a duplicated region within #55, as well as to a fourth region of the chromosome within a more poorly conserved Ig (#61 in Table 1). This repeated region was previously denoted the QUAD repeat and suggested to encode sRNAs (Rudd, K. E. 1999 *Res Microbiol* 150: 653–664). Each of the QUAD repeats contains a short stretch homologous to boxC, a repeat element of unknown function present in 50 copies or more within the genome of *E. coli* (Bachellier, S. et al. 1996 Repeated Sequences In: *Escherichia coli and Salmonella: Cellular and Molecular Biology* eds. F. C. Neidhardt, et al. pp. 2012–2040 American Society for Microbiology, Washington, D.C.). Rudd also has detected transcripts from the QUAD regions. To determine which of the four QUAD genes was being expressed, we designed oligonucleotide probes unique for each of the four repeats. These oligonucleotide probes demonstrated expression for three of the four QUAD genes (#55-I, #55-II, and #61); furthermore, each gave two RNA bands (FIG. 3; Table 2). No signal was detected for the fourth repeat (#43). The #41 Ig region encodes another pair of repeats, PAIR2 (Rudd, K. E. 1999 *Res Microbiol* 150:653–664), and we observed two RNA species, suggesting that each of the repeats may be transcriptionally active. Finally, another repeat region noted by Rudd, PAIR3, is encoded by the #22 Ig region.

Many sRNAs Bind Hfq and Modulate rpoS Expression

Hfq is a small, highly abundant RNA-binding protein first identified for its role in replication of the RNA phage Qβ (Franze de Fernandez, M. et al. 1968 *Nature* 219:588–590; reviewed in Blumenthal, T. and Carmichael, G. G. 1979 *Annu Rev Biochem* 48:525–548). Recently, Hfq has been shown to be involved in a number of RNA transactions in the cell, including translational regulation (rpoS), mRNA polyadenylation, and mRNA stability (ompA, mutS, and miaA) (Muffler, A. et al. 1996 *Genes & Dev* 10:1143–1151; Tsui, H.-C. T. et al. 1997 *J Bacteriol* 179:7476–7487; Vytvytska, O. et al. 1998 *PNAS USA* 95:14118–14123; Hajndsorf, E. and Regnier, P. 2000 *PNAS USA* 97:1501–1505; Vytvytska, O. et al. 2000 *Genes & Dev* 14:1109–1118). Three of the known *E. coli* sRNAs regulate rpoS expression: DsrA RNA and RprA RNA positively regulate rpoS translation, whereas OxyS RNA represses its translation. In all three cases the Hfq protein is required for regulation (Zhang, A. et al. 1998 *EMBO J.* 17:6061–6068; Majdalani, N. et al. 2001 *Mol Microbiol* 39:1382–1394; Sledjeski, D. D. et al. 2001 *J Bacteriol* 183:1997–2005), and binding studies have revealed a direct interaction between Hfq and the OxyS and DsrA RNAs (Zhang, A. et al. 1998 *EMBO J.* 17:6061–6068; Sledjeski, D. D. et al. 2001 *J Bacteriol* 183:1997–2005).

Given the interaction of the Hfq protein with at least three of the known sRNAs, we asked how many of the newly discovered sRNAs are bound by this protein. Hfq-specific antisera was used to immunoprecipitate Hfq-associated RNAs from extracts of cells grown under the conditions used for the Northern analysis. Total immunoprecipitated RNA was examined using two methods. First, RNA was 3'-end labeled and selected RNAs were visualized directly on polyacrylamide gels. Under each growth condition, several RNA species co-immunoprecipitated with Hfq-specific sera but not with preimmune sera, which indicates that many sRNAs interact with Hfq (FIG. 4A). Second, selected RNAs were examined using Northern hybridization to determine whether other known sRNAs and any of our newly discovered sRNAs interact with Hfq. For each sRNA, Hfq binding was examined under growth conditions where the sRNA was most abundant (FIG. 4B; Table 2). sRNAs present in samples using the Hfq antisera but not preimmune sera were concluded to interact with Hfq. Comparison of levels of a selected sRNA relative to the total amount of that sRNA in the extract revealed that many of the sRNAs bound Hfq quite efficiently (>30% bound) (#14, #24, #25, #26, #31, #41, #52-II, Spot42 RNA, and RprA RNA), but other sRNAs bound Hfq less efficiently (<10% bound) (#9, #17, and #52-I), or not at all (#27, #38, #40, 6S RNA, 5S RNA, and tmRNA) (FIG. 4; Table 2).

As mentioned above, at least three of the known sRNAs that interact with Hfq also regulate translation of rpoS, the stationary phase sigma factor. In light of the fact that many of the new sRNAs also interact with Hfq, we examined whether these new sRNAs affect rpoS expression. Plasmids carrying the Ig regions encoding either control sRNAs (pRS-DsrA and pRS-RprA) or many of our novel sRNAs were introduced into an MG1655 Δlac derivative carrying a rpoS-lacZ translational fusion. We then compared expression of the rpoS-lacZ fusion in these cells to cells carrying the control vector by measuring β-galactosidase activity at stationary phase in LB or M63-glucose medium (Table 2). As expected, overproduction of either DsrA RNA or RprA RNA increased rpoS-lacZ expression significantly (Table 2 legend). A number of plasmids (pRS-#24, pRS-#31) led to increased rpoS-lacZ expression, whereas others (pRS-#12, pRS-#14, and pRS-#25) led to decreased expression. These results indicate that the corresponding sRNAs may directly regulate rpoS expression or indirectly affect rpoS expression by altering Hfq activity, possibly by competition. Intriguingly, there is not a complete correlation between Hfq binding and altered rpoS-lacZ expression in these studies.

As another strategy in defining possible functions for the sRNAs, we screened strains carrying the multicopy plasmids for effects on growth in LB medium at various temperatures as well as growth in minimal medium containing a number of different carbon sources. pRS-#25 renders cells unable to grow on succinate in agreement with predictions for #25 RNA interaction with sdh mRNA (discussed below). We were unable to isolate plasmids carrying the #27 Ig region without mutations, indicating that overproduction of this small RNA may interfere with growth. No other growth phenotypes were observed. A caveat for the interpretation of results with the multicopy plasmids is that they contain the full intergenic region, therefore we cannot rule out effects of sequences outside the sRNA genes but within the intergenic regions.

In summary, a multifaceted search strategy to predict sRNA genes was validated by our discovery of 17 novel sRNAs. Northern analysis determined that 44 of 60 candidate regions express RNA transcripts, some of them expressing more than one RNA species. Of these transcripts, 24 were concluded to be 5' untranslated leaders for mRNAs of flanking genes, and another six are predicted to encode new, short ORFs (Tables 1 and 2). The 17 transcripts believed to be novel, functional sRNAs range from 45 nt to 320 nt in length and vary significantly in expression levels and expression profiles under different growth conditions. More than half of the new sRNAs were found to interact with the RNA-binding protein Hfq, indicating that Hfq binding may be a defining characteristic of a family of prokaryotic sRNAs.

Evaluation of Selection Criteria

Three general approaches for predicting sRNA genes were evaluated in this work. In the primary approach, Ig regions were scored for degree and length of conservation between closely related bacterial species followed by examination of sequence features. This approach proved to be very productive in identifying Ig regions encoding novel sRNAs in *E. coli*; more than 30% of the candidates selected primarily on the basis of their conservation proved to encode novel small transcripts. The availability of nearly completed genome sequences for *Salmonella* and *Klebsiella* made this approach possible. Any organism for which the genome sequences of closely related species are known can be analyzed in this way. Comparative genomics of this sort have been used before to search for regulatory sites (for review, see Gelfand, M. S. 1999 *Res Microbiol* 150:755–771), but have not been employed previously to find sRNAs.

Although we found the conservation-based approach to be the most productive in identifying sRNA genes, we note a number of limitations to its use. A high level of conservation is not sufficient to indicate the presence of an sRNA gene. Many of the most highly conserved regions, not unexpectedly, were consistent with regulatory and leader sequences for flanking genes. We also did not analyze any Ig regions where conservation was attributable to sources other than an sRNA. For example, potential sRNAs processed from mRNAs, or any sRNAs encoded by the antisense strand of ORFs or leaders, may have been missed in our approach. We made the assumption that Ig regions must be ≧180 nt to encode an sRNA of ≧60 nt, a 50–60-nt promoter and regulatory region to control expression of the sRNA, as well as regulatory regions for flanking genes. Any sRNA genes in smaller Ig regions would have been overlooked. We also excluded the highly conserved tRNA and rRNA operons from our consideration because of their complexity. It is certainly possible that sRNA genes may be associated with these other RNA genes. In fact, sRNA genes have been predicted to be encoded in at least one tRNA operon. In addition, conservation need not be a property of all sRNAs. We expect sRNAs that play a role in modulating cellular metabolism to be well conserved, as is the case for the previously identified sRNAs. Nevertheless, sRNAs may be encoded within or act upon regions for which there is no homology between *E. coli, Klebsiella*, and *Salmonella* (e.g., in cryptic prophages and pathogenicity islands), and they would be missed by this approach. Only one of 24 Ig regions within the e14, CP4-54, or CP4-6 prophages showed conservation. A few of these Ig regions showed evidence of transcription by microarray analysis, and RNAs have been implicated in immunity regulation in phage P4 (Ghisotti, D. et al. 1992 *Mol Microbiol* 6:3405–3413), which is related to the prophages CP4-54 and CP4-6. Despite the limitations listed above, however, we believe the use of conservation provides a relatively quick identification of the majority of sRNAs.

An alternative genomic sequence-based strategy for identifying sRNAs would be to search for orphan promoter and terminator elements as well as other potential RNA structural elements. Potential promoter elements were generally too abundant to be useful predictors without other information on their expected location and orientation. We found sequences predicted to be rho-independent terminators a more useful indicator of sRNAs; such sequences were clearly present for 13/17 of the sRNAs and 3/6 of the new mRNAs. In a number of cases, it appears that the sRNAs share a terminator with a convergent gene for an ORF. In other cases, either no terminator was detected or it appeared to be in a neighboring ORF. A search using promoter and terminator sequences as the requirements for identifying sRNAs might therefore have found two-thirds of the sRNAs described here. Phage integration target sequences also could be scanned for nearby sRNA genes. Many phage att sites overlap tRNAs (reviewed in Campbell, A. M. 1992 *J Bacteriol* 174: 7495–7499), and ssrA, encoding the tmRNA, has a 3' structure like a tRNA and overlaps the att site of a cryptic prophage (Kirby, J. E. et al. 1994 *J Bacteriol* 176:2068–2081). In this work, we found that the 3' end and terminator of #14 overlaps the previously mapped phage P2 att site (Barreiro, V. and Haggard-Ljungquist, E. 1992 *J Bacteriol* 174:4086–4093). #14 sRNA does not obviously resemble a tRNA, suggesting that the overlap between phage att sites and RNA genes extends beyond tRNAs and related molecules and may be common to additional sRNAs.

Our second approach, high-density oligonucleotide probe array expression analysis, proved to be more useful in confirming the presence of sRNA genes first found by the conservation approach than in identifying new sRNA genes de novo. Further consideration of the location of microarray signal compared to flanking genes as well as analysis of microarray signals after a variety of growth conditions should expand the ability to detect sRNAs in this manner. Under a single growth condition, signal consistent with the RNA identified by Northern analysis was detected for 5/15 of the Ig regions proven to encode new sRNAs and for 4/6 of the new mRNAs. Thus, a similar analysis of microarray data in nonconserved genomic regions might help in the identification of sRNAs missed by the conservation-based approaches. We predict that sRNAs from any organism expressed at reasonably high levels under normal growth conditions will be detected by microarrays that interrogate the entire genome, inclusive of noncoding regions.

One clear limitation in detecting sRNAs with microarray or Northern analyses is the fact that some sRNAs may be expressed only under limited growth conditions or at extremely low levels. We chose three growth conditions to scan our samples. While most of the previously known sRNAs were seen under these conditions, OxyS RNA, which is induced by oxidative stress, was not detectable. For a few of our candidates in which no RNA was detected, it is possible that an sRNA is encoded but is not expressed sufficiently to be detected under any of our growth conditions. Another possible limitation of hybridization-based approaches is that highly structured sRNAs may be refractory to probe generation. sRNA transcripts may not remain quantitatively represented after the fragmentation used in the direct labeling approach here. cDNA labeling also may underrepresent sRNAs because they are a small target for the oligonucleotide primers, and secondary structure can interfere with efficiency of extension.

As our third approach, sRNAs were selected on the basis of their ability to bind to the general RNA binding protein, Hfq. Northern analysis revealed that many of our novel sRNAs interact with Hfq. In preliminary microarray analysis of Hfq-selected RNAs to look for additional unknown sRNAs, DsrA RNA, DicF RNA, Spot42 RNA, #14, #24, #25, #31, #41, and #52-II were detected among those RNAs with the largest difference in levels between Hfq-specific sera and pre-immune sera. This preliminary experiment suggests that microarray analysis of selected RNAs will be very valuable on a genome-wide basis. Interestingly, a large number of genes with leaders and a number of RNAs for operons were found to co-immunoprecipitate with Hfq (including the known Hfq target nlpD-rpoS mRNA (Brown, L. and Elliott, T. 1996 *J Bacteriol* 178:3763–3770). It seems likely that the subset of sRNAs binding a common protein will represent a subset in terms of function; the sRNAs of known function associated with Hfq in our experiments appear to be those involved in regulating mRNA translation and stability. Other sRNAs have been shown to interact with specific prokaryotic RNA-binding proteins, for example, tmRNA with SmpB (Karzai, A. W. et al. 1999 *EMBO J.* 18:3793–3799), and the possibility of other sRNAs interacting with these proteins or other general sRNA-binding proteins should be tested. This approach is adaptable to all organisms, and, in fact, binding to Sm and Fibrillarin proteins has been the basis for identification of several sRNAs in eukaryotic cells (Montzka, K. A. and Steitz, J. A. 1988 *PNAS USA* 85:8885–8889; Tyc, K. and Steitz, J. A. 1989 *EMBO J* 8:3113–3119).

All the criteria we used to identify sRNAs also will detect short genes encoding new small peptides, and we have found six conserved short ORFs. Although our approach was intended to develop methods to identify non-translated genes within the genome, short ORFs also are missing from annotated genome sequences. The combination of a requirement for conservation and/or transcription with sequence predictions for ORFs should add significantly to our ability to recognize short ORFs. Small polypeptides have been shown to have a variety of interesting cellular roles. We expect that the short ORFs we have found are involved in signaling pathways, akin to those of *B. subtilis* peptides that enter the medium and carry out cell-cell signaling (reviewed in Lazazzera, B. A. 2000 *Curr Opin Microbiol* 3:177–182).

Characteristics and Functions of New sRNAs

The current work serves as a blueprint for the prediction, detection, and characterization of a large group of novel sRNAs. We have definitive information on characteristics that provide information regarding the cellular roles of these new sRNAs. Several known sRNAs that bind the Hfq protein act via base pairing to target mRNAs. The finding that a number of our new sRNAs bind Hfq indicates a similar mechanism of action for this subset of sRNAs. We searched the *E. coli* genome for possible complementary target sequences and examined phenotypes associated with multicopy plasmids containing new sRNA genes. Intriguingly, #25, an sRNA preferentially expressed in minimal medium, has extended complementarity to a sequence near the start of sdhD, the second gene of the succinate dehydrogenase operon. When the #25 Ig region is present on a multicopy plasmid, it interferes with growth on succinate minimal medium (Table 2), consistent with #25 sRNA acting as an antisense RNA for sdhD. Complementarity to many target mRNAs was found for a number of other novel sRNAs, confirming the validity of this analysis.

As outlined in the evaluation of each of our approaches, we do not expect our searches have been exhaustive. sRNAs also have been detected by others using a variety of approaches. The sRNA encoded by #38 was independently identified as a regulatory RNA (CsrC RNA; T. Romeo, pers. comm.), and others have found additional sRNAs using variations of the approaches used here (Argaman, L. et al. 2001. *Curr. Biol.* in press). Nevertheless, we think it unlikely that there are many more than 50 sRNAs encoded by the *E. coli* chromosome and by closely related bacteria. We expect such sRNAs to be present and playing important regulatory roles in all organisms. Using the approaches described here, it is feasible to search all sequenced organisms for these important regulatory molecules. We anticipate that study of the expanded list of sRNAs in *E. coli* will allow a more complete understanding of the range of roles played by regulatory sRNAs.

EXAMPLE 1

Computer Searches

Ig regions are defined here as sequences between two neighboring ORFs. We compared Ig regions of ≧180 nt against the NCBI Unfinished Microbial Genomes database (Worldwide Web at ncbi.nlm.nih.gov/Microb_blast/unfinishedgenome.html) using the BLAST program (Altschul, S. F. et al. 1990 *J Mol Biol* 215:403–410). *Salmonella enteritidis* sequence data were from the University of Illinois, Department of Microbiology (Worldwide Web at salmonella.org). *Salmonella typhi* and *Yersinia pestis* sequence data were from the Sanger Centre (www.sanger.ac.uk/Projects/S_typhi/ and sanger.ac.uk/Projects/Y_pestis/). *Salmonella typhimurium*, *Salmonella paratyphi*, and *Klebsiella pneumoniae* sequences were from the Washington University Genome Sequencing Center.

Each Ig region was rated based on the best match to *Salmonella* or *K pneumoniae* species. Ig regions containing previously identified sRNAs were rated 5 (each of them met the criteria to be rated 4). Ig regions were rated 4 if the raw BLAST score was >200 (hatched bars in FIG. 1) or 80–200 (double-diagonal bars in FIG. 1) extending for >80 nt; 3 if the raw BLAST score was 80–200 (double-diagonal bar) extending for 60–80 nt; 2 if the raw BLAST score was 50–80 (diagonal bar) extending for >65 nt; and 1 if the raw BLAST score was <50 (diagonal-dash, solid or none) or <65 nt. The location of the longest conserved section(s) within each Ig and the number of matches to the NCBI Unfinished Microbial database were recorded. Note that the computer searches were done from May 2000 to December 2000; more sequences are expected to match as the database continues to expand. The identity and orientation of genes flanking each Ig region were determined from the Colibri database (using http://forgenolist.pasteur.fr/Colibri). Ig regions that the Colibri database predicted to be <180 nt in length and Ig regions containing tRNA and/or rRNAs were rated 0 and removed from further consideration.

Strains and Plasmids

Strains were grown at 37° C. in Luria-Bertani (LB) medium or M63 minimal medium supplemented with 0.2% glucose and 0.002% vitamin B1 (Silhavy, T. J. et al. 1984 *Experiments with gene fusions* Cold Spring Harbor Laboratory, Cold Spring Harbor, N.Y.) except for phenotype testing of strains carrying multicopy plasmids as described below. Ampicillin (50 µg/ml) was added where appropriate. *E. coli* MG1655 was the parent for all strains used in this study. MG1655 Δlac (DJ480, obtained from D. Jin, NCI), was lysogenized with a λ phage carrying an rpoS-lacZ translational fusion (Sledjeski, D. D. et al. 1996 *EMBO J.* 15:3993–4000) to create strain SG30013.

To generate clones containing the Ig region of each candidate (pCR-#N where N refers to candidate number; see Table 1), Ig regions were amplified by PCR from a MG1655 colony and cloned into the pCRII vector using the TOPO TA cloning kit (Invitrogen). Oligonucleotides were designed so the entire conserved region and in most cases the full Ig region was included. In a few cases, repeated sequences or other irregularities required a reduction in the Ig regions cloned. See Table 3 for a list of all oligonucleotides used in this paper. Ig regions encoding sRNAs also were cloned into multicopy expression vectors (pRS-#N) in which each Ig region is flanked by several vector-encoded transcription terminators. To generate pRS-#N plasmids, pCR-#N plasmids were digested with BamHI and XhoI and the Ig-containing fragments were cloned into the BamHI and SalI sites of pRS1553 (Pepe, C. M. et al. 1997 *J Mol Biol* 270:14–25), replacing the lacZ-α peptide. To construct pBS-spot42, the Spot42-containing fragment was amplified by PCR from K12 genomic DNA, digested with EcoRI and BamHI and cloned into corresponding sites in pBluescript II SK⁺ (Stratagene). All DNA manipulations were carried out using standard procedures. All clones were confirmed by sequencing.

TABLE 3

Oligonucleotides

| Oligo Name | Sequence | SEQ ID NO | Candidate Number |
|---|---|---|---|
| KW-39 | GCGCCTCGTTATCATCCAAAATACG | 32 | #1 |
| KW-40 | GTCGCCCAGCCAATGCTTTCAGTCG | 33 | |
| KW-41 | ATTGATCGCACACCTGACAGCTGCC | 34 | #2 |
| KW-42 | GTTGTCACCCTGGACCTGGTCGTAC | 35 | |
| KW-43 | TGACCGCGATTTGCACAAAATGC | 36 | #3 |
| KW-44 | ACTCTTAAATTTCCTATCAAAACTCGC | 37 | |
| KW-45 | GGTATTTTCAGAGATTATGAATTGCCG | 38 | #4 |
| KW-46 | TCACCTCTCCTTCGAGCGCTACTGG | 39 | |
| KW-47 | AATGCTCTCCTGATAATGTTAAACTT | 40 | #5 |
| KW-48 | GGTTAGCTCCGAAGCAAAAGCCGGAT | 41 | |
| KW-49 | TAATTCCTTTCAAATGAAACGGAGC | 42 | #6 |
| KW-50 | GGACTCCCTCATTATAATTACTGG | 43 | |
| KW-51 | CTCCTTAAACAAGGACATTAGTCTACG | 44 | #7 |
| KW-52 | ATTCACCTTACCTAATTTGATTCTTCC | 45 | |
| KW-123 | CCATCGCTTGACGTTGCATTTCACCTGC | 46 | #8 (probes) |
| KW-124 | GTCGGCGTCGTACGAATCAATTGTGC | 47 | |
| KW-125 | GCACAATTGATTCGTACGACGCCGAC | 48 | |
| KW-55 | TAAGGATAATATTGCAGATCGTAAG | 49 | #9 |
| KW-56 | ATCATCAAACAGCAACTTGCCC | 50 | |
| KW-57 | TGTCCTTCTCCTGCAAGAGAATTATT | 51 | #10 |
| KW-58 | GCTAATAATAATGTCTTTTTCGCTCC | 52 | |
| FR-100 | GCTTTTGTGAATTAATTTGTATATCGAAGCG | 53 | #11 |
| FR-101 | TATTAATACCCTCTAGATTGAGTTAATC | 54 | |
| FR-102 | CGATTTACCTCACTTCATCGCTTTCAG | 55 | #12 |
| FR-103 | TGATCCTGACTTAATGCCGCAAGTTC | 56 | |
| FR-104 | GCTTATCTCCGGCACTCTCAGTGGCTTAGCTCTTGAAGG | 57 | (probe) |
| FR-105 | TTGCTCACATCTCACTTTAATCGTGCTC | 58 | #13 |
| FR-106 | ATATTCCACCAGCTATTTGTTAGTGAATAAAAGG | 59 | |
| FR-107 | TGATTAATTTCGATTATTTTTCCCGGATGG | 60 | #14 |
| FR-108 | ATTAGAAACAGGAAGCCCCTCAGTCGAG | 61 | |
| FR-109 | TTATTTTCCCCGGAAGCACATTCACTTCAC | 62 | #15 |
| FR-110 | TGATCTATTGCACAACGAGGAAGC | 63 | |
| FR-111 | TGCTTACTCATCAAAAGTAGCGCCAGATTC | 64 | #16 |
| FR-112 | TAATCGACGGACGATAGATAATTCCTG | 65 | |
| FR-113 | CCAATGTGTCGCCTTTTTCAACTTTCCG | 66 | #17 |
| FR-114 | CGATTTATGAGAATAAATACTCATTTAAGGGTG | 67 | |

TABLE 3-continued

Oligonucleotides

| Oligo Name | Sequence | SEQ ID NO | Candidate Number |
|---|---|---|---|
| FR-115 | AAATCCGACTTTAGTTACAACATAC | 68 | #18 |
| FR-116 | GACCAGACCTTCTTGATGATGGGCAC | 69 | |
| KW-69 | CGACCTCAATTCCACGGGATCTGG | 70 | #19 |
| KW-70 | ATTTAGCTGTAGTAATCACTCGCCG | 71 | |
| KW-71 | GGTCTCCTTAGCGCCTTATTGCG | 72 | #20 |
| KW-72 | CGCCCACATGCTGTTCTTATTATTCCC | 73 | |
| KW-73 | TTTATGACACCTGCCACTGCCGTC | 74 | #21 |
| KW-74 | CTGTCAAGTTATCTGTTTGTTAAGTCAAGC | 75 | |
| KW-126 | GCTGTGAAGCACCTGCGTTGCTCATG | 76 | #22 |
| KW-127 | GCTGTGAAACACCTGCATTTACGGCCACGG | 77 | (probes) |
| KW-128 | CCGTGGCCGTAAATGCAGGTGTTTCACAGC | 78 | |
| KW-77 | CCTTTCGCAATTGACTGAAACAC | 79 | #24 |
| KW-78 | GGCTAGACCGGGGTGCGCG | 80 | |
| KW-79 | AAGGTGGTTATTTACACCTTAGCG | 81 | #25 |
| KW-80 | GTCCTCTTTGGGGTAAATGTC | 82 | |
| KW-81 | AATGCTCCGGTTTCATGTCATC | 83 | #26 |
| KW-82 | TAGTTCCTTCTCACCCGGAG | 84 | |
| FR-117 | CACAAGGGCGCTTTAGTTTGTTTTCCG | 85 | #27 |
| FR-118 | ATCCCCTGAGAGTTTAATTTTCGTCAAG | 86 | |
| KW-85 | TAATTCGTCGTAATTCGTCCTCC | 87 | #28 |
| KW-86 | CTCTGCCTTCCTGTTTTTGTTGTG | 88 | |
| FR-119 | AAACGCATTTGCAACTGTCGGCGCTTTTCC | 89 | #29 |
| FR-120 | CTTGTTACCTCAAAAAATCACAGTGCTCG | 90 | |
| FR-121 | GCAGTCGGTGATGCTGGATTTGCCCTG | 91 | #30 |
| FR-122 | GTTTTTTTACGGGTAAGCCGCAACGACCATTG | 92 | |
| FR-123 | TAGTAGATAAGTTTTAGATAAC | 93 | #31 |
| FR-124 | TAAAACTGAAGTTGCCCTGAAAATG | 94 | |
| FR-125 | TGATGAGTGGTTCTGCAAGAGG | 95 | #32 |
| FR-126 | TAAAAGACAGATTACCTGGCCTG | 96 | |
| FR-127 | CGGACTACCTCAAAATAAAGCTTTATATACG | 97 | #33 |
| FR-128 | GTCATGATACCTTGATTAAAAAACAAACAGC | 98 | |
| FR-129 | GGCTATAATGCGCACATAACCTCTTG | 99 | #34 |
| FR-130 | AATCTTTTCTTATTTTTTGGCTAACGAATAGCC | 100 | |
| FR-131 | GTCCAACTTTTTGGGGTCAGTACAAACTTTG | 101 | #35 |
| FR-132 | TAATAACGCCGTTATTAAATAGCCTGCC | 102 | |
| FR-133 | TAAGCAACGTCTGCTTACTGCCCCTC | 103 | #36 |

TABLE 3-continued

Oligonucleotides

| Oligo Name | Sequence | SEQ ID NO | Candidate Number |
|---|---|---|---|
| FR-134 | GTGATGGCTTCTGATAAAGATAAATTTATAGCC | 104 | |
| FR-135 | TAACAGGCTAAGAGGGGC | 105 | #37 |
| FR-136 | ATTGCCACTCTTCTTGATCAAATAACCG | 106 | |
| FR-137 | AATGCGTCTGTTGATAATTCAAATTAGTC | 107 | #38 |
| FR-138 | TAGCCGTTTTATTCAGTATAGATTTGCG | 108 | |
| KW-89 | GTTCGTCGGTAACCCGTTTCAGC | 109 | #39 |
| KW-90 | ATGGCTTAAAGAGAGGTGCC | 110 | |
| KW-91 | CGTACTTTAAAGGGAGAATGAC | 111 | #40 |
| KW-92 | GTGCTTCCTCATTATGGTGACG | 112 | |
| KW-93 | GAATGGAGGGAGATTACACG | 113 | #41 |
| KW-94 | CCTTAGTGGGTAAACGCTTAC | 114 | |
| KW-95 | CTTTCAGGCAGCTAAGGAAAG | 115 | #42 |
| KW-96 | CAATATGTATTATTGATTGAGTAAACGGG | 116 | |
| KW-97 | CCTCTTCCAGGAATAATCCC | 117 | #43 |
| KW-98 | CGGAAAGCGGTTCACAGATC | 118 | |
| KW-132 | CTCGTAAGTTTCGCAGCTTATTA | 119 | #43 (probe) |
| KW-99 | TGAAATTCCTGTCCGACAGG | 120 | #44 |
| kW-100 | GCACTACCGCAATGTTATTGC | 121 | |
| KW-101 | GCTTACCCAATAAATAGTTACACG | 122 | #45 |
| KW-102 | TAAAACCTGTCACAAATCACAAA | 123 | |
| KW-103 | GTGGCCTGCTTCAAACTTTCG | 124 | #46 |
| KW-104 | GTAAAGTCTAGCCTGGCGGTTCG | 125 | |
| FR-139 | TAATTCTGGTACGCCTGGCAGATATTTTGCC | 126 | #47 |
| FR-140 | ATCAACCTCAAAAGGGAAATCGGG | 127 | |
| KW-105 | TAACTTGTTGTAAGCCGGATCGG | 128 | #48 |
| KW-106 | TGAAGCATCTATCGCCGGTTGCG | 129 | |
| KW-107 | GATTAGAAATCCTTTTGAAAGCGCATTG | 130 | #49 |
| KW-108 | CTTATTGGGCACCGCAATGG | 131 | |
| KW-109 | CGAACACAATAAAGATTTAATTCAGCC | 132 | #50 |
| KW-110 | CTGATGCTACTGTGTCAACG | 133 | |
| KW-111 | AATAATCAGACATAGCTTAGGC | 134 | #51 |
| KW-112 | GCCGTGATGGTTTTCGCGTTC | 135 | |
| KW-113 | TATTTTCCTCCCGCGCTAAAG | 136 | #52 |
| KW-114 | TTCAGCTGATGACCACCACGCTT | 137 | |
| KW-115 | GAGTTGTCAGAGCAGGATGATTC | 138 | #53 |
| KW-116 | TATCTGCGCTTATCCTTTATGG | 139 | |

TABLE 3-continued

Oligonucleotides

| Oligo Name | Sequence | SEQ ID NO | Candidate Number |
|---|---|---|---|
| KW-117 | CCTTTACGGTGATAACCGTCGCG | 140 | #54 |
| KW-118 | CTGACAAGCCTCTCATTCTCTTGTC | 141 | |
| KW-119 | GAGAATTATCGAGGTCCGGTATC | 142 | #55 |
| KW-120 | CTACGCGTTAGCGATAGACTGC | 143 | |
| FR-141 | AGGCTTACTAAGAACACCAGGGGAGGGGAA | 144 | probe for 55-I |
| FR-142 | AGTCATAAGCTTCCCCGCTTACTAAGACTA | 145 | probe for 55-II |
| KW-121 | CCTCAAATCGGCCATAATAACC | 146 | 56 |
| KW-122 | TAAACACCGTCGTCAGAAATGC | 147 | |
| FR-143 | TAGACTTTTATCCACTTTATTGCTG | 148 | #57 |
| FR-144 | GTGTGCCTTTCGGCGATATGGCGTG | 149 | |
| FR-145 | CCTTTACGTGGGCGGTGATTTTGTC | 150 | #58 |
| FR-146 | TAGCTTTGCTCCTGGATGTTTGCC | 151 | |
| FR-147 | GCTGTAATTTATTCAGCGTTTGTACATACG | 152 | #59 (probe) |
| FR-148 | TCAGTCAACTCGCTGCGGCGTGTTAC | 153 | #60 |
| FR-149 | CTTATTGTTGCTTAGTTAGGGTAGTCAC | 154 | |
| KW-131 | CAGTCAGTCTCAGGGGAGGAGCAATC | 155 | #61 (probe) |
| KW-59 | TGAATGCACAATAAAAAAATCCCGACCCTG | 156 | For DsrA |
| KW-60 | AGTCGCGCAGTACTCCTCTTACCAG | 157 | Ig region |
| KW-63 | TAATTTCTCATCAGGCGGCTCTGC | 158 | for RprA |
| KW-64 | TAACATTATCAGCCTGCTGACGGC | 159 | Ig region |
| sp42-5'-1 | GGCCGAATTCGTAGGGTACAGAGGTAAG | 160 | for cloning |
| sp42-3'-1 | GGCCGGATCCGTCATTACTGACTGGGCGG | 161 | pBSspot42 |

RNA Analysis

RNA for Northern analysis was isolated directly from ~3×10$^9$ cells in exponential growth (OD$_{600}$=0.2–0.4) or stationary phase (overnight growth) as described previously (Wassarman, K. M. and Storz, G. 2000 Cell 101:613–623). Five-μg RNA samples were fractionated on 10% polyacrylamide urea gels and transferred to Hybond N membrane as described previously (Wassarman, K. M. and Storz, G. 2000 Cell 101:613–623). For Northern analysis of candidate regions, double-stranded DNA probes were generated by PCR from a colony of MG1655 cells or from the pCR-#N plasmids with oligonucleotides used for cloning the pCR-#N plasmids. PCR amplification was done with 52° C. annealing for 30 cycles in 1×PCR buffer (1 mM each dATP, dGTP, and dTTP; 2.5 μM dCTP; 100 μCi [α$^{32}$P] dCTP; 10 ng plasmid; 1 unit taq polymerase) (Perkin Elmer). Probes were purified over G-50 microspin columns (Amersham Pharmacia Biotech) prior to use. Northern membranes were prehybridized in a 1:1 mixture of Hybrisol I and Hybrisol II (Intergen) at 40° C. DNA probes with 500 μg sonicated salmon sperm DNA were heated for 5 min to 95° C., added to prehybridization solution, and membranes were hybridized overnight at 40° C. Membranes were washed by rinsing twice with 4×SSC/0.1% SDS at room temperature followed by three washes with 2×SSC/0.1% SDS at 40° C. Northern blot analysis using RNA probes was done as described previously (Wassarman, K. M. and Steitz, J. A. 1992 Mol Cell Biol 12:1276–1285). RNA probes were generated by in vitro transcription according to manufacturer protocols (Roche Molecular Biochemicals) from pCR-#N plasmids linearized with EcoRV or HinDIII using SP6 RNA polymerase or T7 RNA polymerase, respectively; pBS-6S (pGS0112; Wassarman, K. M. and Storz, G. 2000 Cell 101:613–623) or pBS-spot42 were linearized with EcoRI using T3 RNA polymerase; pGEM-5S (pG5019; Altuvia, S. et al. 1997 *Cell* 90:43–53) or pGEM-10Sa (Altuvia, S. et al. 1997 *Cell* 90:43–53) were linearized with EcoRI using SP6 RNA polymerase. Oligonucleotide probes were labeled by polynucleotide kinase according to manufacturer protocols (New England Biolabs) using [$\gamma^{32}$P]ATP (>5000 Ci/mmole; Amersham Pharmacia Biotech). For oligonucleotide probes, Northern membranes were prehybridized in Ultrahyb (Ambion) at 40° C. followed by addition of labeled oligonucleotide probe and hybridization overnight at 40° C. Membranes were washed twice with 2×SSC/0.1% SDS at room temperature followed by two washes with 0.1×SSC/0.1% SDS at 40° C. for 15 minutes each.

Immunoprecipitation

Immunoprecipitations were carried out using extracts from cells in exponential growth ($OD_{600}$=0.2–0.4) or stationary phase (overnight growth) as described previously (Wassarman, K. M. and Storz, G. 2000 *Cell* 101:613–623), using rabbit antisera against the Hfq protein or preimmune serum. After immunoprecipitation, RNA was isolated from Protein A Sepharose-antibody pellets by extraction with phenol:chloroform:isoamyl alcohol (50:50:1) followed by ethanol precipitation. RNA was examined on gels directly after 3' end labeling or analyzed by Northern hybridization after fractionation on 10% polyacrylamide urea gels as described previously (Wassarman, K. M. and Storz, G. 2000 *Cell* 101:613–623).

rpoS-lacZ Expression

Effects on rpoS-lacZ expression by multicopy plasmids containing the novel sRNAs were determined from a single colony of SG30013 transformed with pRS-#N, grown for 18 h in 5 ml of LB-ampicillin medium or M63-ampicillin medium supplemented with 0.2% glucose at 37° C. β-galactosidase activity in the culture was assayed as described previously (Zhou, Y.-N. and Gottesman, S. 1998 *J Bacteriol* 180:1154–1158). The numbers provided in Table 2 were calculated as the ratio between pRS-#N and the pRS1553 vector control.

Phenotype Testing

To test carbon source utilization or temperature sensitivity associated with the multicopy plasmids containing the novel sRNAs, a single colony of MG1655 transformed with a given pRS-#N was grown for 6 hours in 5 ml LB-ampicillin medium at 37° C. Then 10 µl of serial dilutions ($10^{-2}$, $10^{-4}$, and $10^{-6}$) were spotted on M63-ampicillin plates containing 0.2% of the carbon source being tested (glucose, arabinose, lactose, glycerol, ribose, or succinate) and grown at 37° C.; or on LB plates incubated at room temperature or 42° C. Plates were analyzed after both 1 and 2 days. Failure to grow in Table 2 indicates an efficiency of plating of <$10^{-3}$.

Microarray Analysis

RNA for microarray analysis was isolated using the MasterPure RNA purification kit according to the manufacturer protocols (Epicentre) from MG1655 cells grown to $OD_{600}$=0.8 in LB medium at 37° C. DNA was removed from RNA samples by digestion with DNase I for 30 min at 37° C. Probes for microarray analysis were generated by one of two methods: direct labeling of enriched mRNA or generation of labeled cDNA.

To generate direct labeled RNA probes, mRNA enrichment and labeling was done as described in the Affymetrix expression handbook (Affymetrix). Oligonucleotide primers complementary to 16S and 23S rRNA were annealed to total RNA followed by reverse transcription to synthesize cDNA strands complementary to 16S and 23S rRNA species. 16S and 23S were degraded with RNase H followed by DNase I treatment to remove cDNA and oligonucleotides. Enriched RNA was fragmented for 30 min at 95° C. in 1×T4 polynucleotide kinase buffer (New England Biolabs), followed by labeling with γ-S-ATP and T4 polynucleotide kinase and ethanol precipitation. The biotin label was introduced by resuspending RNA in 96 µl of 30 mM MOPS (pH 7.5), 4 µl of a 50 mM Iodoacetylbiotin solution, and incubating at 37° C. for 1 hr. RNA was purified using the RNA/DNA Mini Kit according to manufacturer protocols (QIAGEN).

To generate cDNA probes, 5 µg of total RNA was reverse transcribed using the Superscript II system for first strand cDNA synthesis (Life Technologies) and 500-ng random hexamers. RNA and primers were heated to 70° C. and cooled to 25° C.; reaction buffer was then added, followed by addition of Superscript II and incubation at 42° C. RNA was removed by RNase H and RNase A. The cDNA was purified using the Qiaquick cDNA purification kit (QIAGEN) and fragmented by incubation of up to 5 µg cDNA and 0.2 U DNase I for 10 min at 37° C. in 1× one-phor-all buffer (Amersham-Pharmacia Biotech). The reaction was stopped by incubation for 10 min at 99° C., and fragmentation was confirmed on a 0.7% agarose gel to verify that average length fragments were 50–100 nt. Fragmented cDNA was 3'-end-labeled with terminal transferase (Roche Molecular Biochemicals) and biotin-N-6-ddATP (DuPont/NEN) in 1×TdT buffer (Roche Molecular Biochemicals) containing 2.5 mM cobalt chloride for 2 hours at 37° C.

Hybridization to microarrays and staining procedures were done according to the Affymetrix expression manual (Affymetrix). The arrays were read at 570 nm with a resolution of 3 µm using a laser scanner.

The expression of genes was analyzed using the Affymetrix Microarray Suite 4.01 software program. Detection of transcripts in intergenic regions was done using the intensities of each probe designed to be a perfect match and the corresponding probe designed to be the mismatch. If the perfect match probe showed an intensity that was 200 units higher than the mismatch probe, the probe pair was called positive. Two neighboring positive probe pairs were considered evidence of a transcript. The location and length of the transcripts were estimated based on the first and last identified positive probe pair within an Ig region.

While the present invention has been described in some detail for purposes of clarity and understanding, one skilled in the art will appreciate that various changes in form and detail can be made without departing from the true scope of the invention. All patents, patent applications and publications referred to above are hereby incorporated by reference.

What is claimed is:

1. An isolated polynucleotide comprising Candidate #25 having SEQ ID NO:5, or its complement, or a polynucleotide having at least about 95% identity thereto and having a function of binding Hfq, wherein said polynucleotide is separated from flanking genes yhhX and yhhY.

* * * * *